(12) United States Patent
Gossard et al.

(10) Patent No.: US 11,517,640 B2
(45) Date of Patent: Dec. 6, 2022

(54) ADSORBENT AND PHOTOCATALYTIC DECONTAMINATION GEL, AND METHOD FOR DECONTAMINATING SURFACES USING SAID GEL

(71) Applicant: COMMISSARIAT À L'ÉNERGIE ATOMIQUE ET AUX ÉNERGIES ALTERNATIVES, Paris (FR)

(72) Inventors: Alban Gossard, Avignon (FR); Fabien Frances, Rousson (FR); Célia Lepeytre, Rocheford du Gard (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 826 days.

(21) Appl. No.: 16/316,686

(22) PCT Filed: Jul. 12, 2017

(86) PCT No.: PCT/FR2017/051922
§ 371 (c)(1),
(2) Date: Jan. 10, 2019

(87) PCT Pub. No.: WO2018/011525
PCT Pub. Date: Jan. 18, 2018

(65) Prior Publication Data
US 2020/0179546 A1   Jun. 11, 2020

(30) Foreign Application Priority Data
Jul. 13, 2016   (FR) ...................................... 1656758

(51) Int. Cl.
*A61L 2/23*       (2006.01)
*A01N 25/04*   (2006.01)
(Continued)

(52) U.S. Cl.
CPC ................ *A61L 2/23* (2013.01); *A01N 25/04* (2013.01); *A01N 59/00* (2013.01); *A61L 2/26* (2013.01);
(Continued)

(58) Field of Classification Search
CPC .......... A61L 2/23; A61L 2/26; A61L 2202/13; A61L 2202/20; A01N 25/04; A01N 59/00
See application file for complete search history.

(56) References Cited

U.S. PATENT DOCUMENTS

| | | | |
|---|---|---|---|
| 7,713,357 B2 | 5/2010 | Faure et al. | |
| 7,718,010 B2 | 5/2010 | Faure et al. | |
| 8,636,848 B2 | 1/2014 | Faure et al. | |
| 9,451,765 B2 | 9/2016 | Cuer et al. | |

(Continued)

FOREIGN PATENT DOCUMENTS

| | | |
|---|---|---|
| DE | 10 2004 033620 A1 | 2/2006 |
| DE | 10 2004 033621 A1 | 2/2006 |

(Continued)

OTHER PUBLICATIONS

Office action issued for Japanese application No. 2019-501703 dated Jun. 18, 2021 and translation thereof.

(Continued)

*Primary Examiner* — Sean E Conley
(74) *Attorney, Agent, or Firm* — Pearne & Gordon LLP

(57) ABSTRACT

An adsorbent and photocatalytic decontamination gel consisting of a colloidal solution comprising, preferably consisting of: 8% to 30% by weight, preferably 10% to 30% by weight, more preferably 15% to 20% by weight, better still 15% to 20% by weight, the value 15% being excluded, even better still 16% to 20% by weight, for example 20% by weight of $TiO_2$, optionally doped, relative to the weight of the gel; optionally 0.01% to 10% by weight, preferably 0.1% to 5% by weight, relative to the weight of the gel, of at least one dye and/or of at least one pigment; optionally 0.1% to (Continued)

2% by weight, relative to the weight of the gel, of at least one surfactant; optionally 0.05% to 5% by weight, preferably 0.05% to 2% by weight, relative to the weight of the gel, of at least one superabsorbent polymer; and the balance of solvent.

36 Claims, 5 Drawing Sheets

(51) Int. Cl.
    *A01N 59/00*    (2006.01)
    *A61L 2/26*    (2006.01)

(52) U.S. Cl.
    CPC ....... *A61L 2202/13* (2013.01); *A61L 2202/20* (2013.01)

(56) References Cited

U.S. PATENT DOCUMENTS

| | | |
|---|---|---|
| 2004/0245496 A1 | 12/2004 | Taoda |
| 2013/0171024 A1 | 7/2013 | Cuer et al. |
| 2016/0050911 A1 | 2/2016 | Ludwig et al. |
| 2016/0057993 A1 | 3/2016 | Ludwig et al. |
| 2017/0239694 A1 | 8/2017 | Ludwig et al. |

FOREIGN PATENT DOCUMENTS

| | | |
|---|---|---|
| DE | 10 2007 014875 A1 | 10/2008 |
| DE | 10 2007 025562 A1 | 12/2008 |
| EP | 1 174 392 A1 | 1/2002 |
| FR | 2 789 591 A1 | 8/2000 |
| FR | 2827530 A1 | 1/2003 |
| FR | 2891470 A1 | 4/2007 |
| JP | H11-101894 A | 4/1999 |
| JP | 2003171693 A | 6/2003 |
| JP | 2013-532160 A | 8/2013 |
| WO | 96/23051 A1 | 8/1996 |
| WO | 2012001046 A1 | 1/2012 |
| WO | 2014/154817 A1 | 10/2014 |
| WO | 2014/154818 A1 | 10/2014 |

OTHER PUBLICATIONS

International Search Report for International Application No. PCT/FR2017/051922, dated Oct. 23, 2017.
Written Opinion for International Application No. PCT/FR2017/051922, dated Oct. 23, 2017.
Preliminary French Search Report for Application No. FR 1656758, dated Mar. 20, 2017.
International Preliminary Report Patentatiblity for PCT/FR2017/051922 dated Sep. 12, 2018.

ADSORBENT AND PHOTOCATALYTIC DECONTAMINATION GEL, AND METHOD FOR DECONTAMINATING SURFACES USING SAID GEL

CROSS-REFERENCE TO RELATED APPLICATIONS

This is a National Stage application of PCT international application PCT/FR2017/051922, filed on Jul. 12, 2017, which claims the priority of French Patent Application No. 16 56758, filed Jul. 13, 2016, both of which are incorporated herein by reference in their entirety.

TECHNICAL FIELD

The subject of the present invention is an adsorbent and photocatalytic decontamination gel useful for decontaminating surfaces.

The present invention further pertains to a method for decontaminating surfaces using this gel.

The method and gel of the invention allow the decontamination of all kinds of surfaces such as surfaces made of metal, plastic and mineral materials such as glassy materials.

The method and gel of the invention particularly apply inter alia to the decontamination of surfaces of porous materials such as cement materials like mortars and concretes; bricks; plaster; and natural stone.

The method and gel of the invention also allow the removal of all kinds of contaminating species (or contaminants) and in particular ionic, chemical, biological or nuclear, radioactive contaminating species.

For example, if the contaminating species removed by the gel are ionic contaminating species, then the gel is termed an ionic decontamination gel.

In general, the technical field of the invention can therefore be defined as the field of surface decontamination with a view to removing pollutants, contaminants found on this surface and optionally underneath this surface, the presence of which on or under these surfaces is not desirable.

STATE OF THE PRIOR ART

Decontamination gels were particularly developed for surface radiological decontamination, notably when dismantling nuclear plants.

For example, for nuclear decontamination, gelled formulations which overcome problems related to the powdery nature of the dry waste and increase the efficacy of methods using a gel have been the subject of documents [1] and [2].

These documents [1] and [2] describe inorganic colloidal gels called «vacuumable gels», specifically formulated to be sprayed, then to fractionate on drying whilst trapping and confining the radioactive contamination in the form of flakes that can be vacuumed and stored.

These colloidal gels comprise an inorganic viscosifying agent containing silica or alumina, one or more active decontamination agents and optionally one or more surfactant(s).

More specifically, document [1] describes a gel composed of a colloidal solution comprising an inorganic viscosifying agent, generally silica or alumina, an active treatment agent which can be an acid or inorganic base for example such as sodium hydroxide or potassium hydroxide, and optionally an oxidizing agent having a standard redox potential $E_0$ higher than 1.4 V in a strong acid medium such as Ce(IV), Co(III) or Ag(II).

Document [2] describes a gel composed of a colloidal solution comprising an organic viscosifying agent, generally silica or alumina, a surfactant, an acid or inorganic base, and optionally an oxidizing agent having a standard redox potential $E_0$ higher than 1.4 V in a strong acid medium such as Ce(IV), Co(III) or Ag(II).

The rheology of these inorganic colloidal gels, on account of the different constituents included in their composition, enables them to be sprayed onto a contaminated surface, followed by adhering thereof to this surface, even a vertical surface, without run-off.

This therefore allows extended contact between the contaminant and the active decontamination agent, without detriment to the mechanical properties of the substrate.

After being sprayed the gel dries, fractionates and produces dry residues called «flakes», adhering to the substrate that can then be removed by brushing and/or vacuuming to be directly packaged.

Decontamination methods using these vacuumable gels are therefore dry route decontamination methods not generating any liquid effluent and few dry solid residues. These dry solid residues on average only represent one quarter of the amount of gel initially sprayed. In addition, these methods limit operator exposure time to radioactive contamination since they are easily applied by spraying followed by vacuuming of the dry residues, the presence of the operator therefore not being required during drying of the gel.

The gels described in documents [1] and [2] can notably be qualified as «ionic» decontamination gels, since the pollution they are intended to remove is particularly in ion form.

These gels owe their efficacy to chemical attack of the surface to be decontaminated, through the presence of an acid or the presence of a powerful organic agent such as cerium oxide.

Yet, in some cases, it is necessary to preserve the surface to be decontaminated and to prevent corrosion thereof, whilst ensuring extraction, removal of the pollutants, contaminants present on this surface.

In addition, after drying and vacuuming these gels, the gel flakes may release polluting, contaminating species trapped and captured by the gels when these dry gel flakes come into contact with water.

The polluting species are simply «encapsulated» in the dry gel flakes which therefore do not have any «confining» property.

The decontamination gels such as those described in documents [1] and [2] therefore have the disadvantage of causing corrosion, deterioration of the surface to be decontaminated, and of forming flakes that do not confine the contaminating, polluting species and may release these polluting species, in particular if the dry gel flakes come into contact with a liquid such as water.

In the light of the foregoing, there if therefore a need for an «ionic» decontamination gel which allows efficient transfer of ionic contaminating species without corroding attacking, deteriorating this surface.

There is also a need for said «ionic» decontamination gel which ensures confining of the contaminating, polluting species within the dry gel, after treatment of the contaminated surfaces, and which prevents release of these polluting, contaminating species in particular if the dry gel flakes come into contact with a liquid such as water.

Other gels have been developed to carry out biological or chemical decontamination of surfaces.

Said biological decontamination gels are the subject of documents [3] and [4].

As active biological decontamination agents, these gels contain powerful oxidizing agents and more particularly sodium hypochlorite.

More specifically, document [3] describes a biological decontamination gel composed of a colloidal solution comprising at least one inorganic viscosifying agent, generally silica or alumina, at least one active biological decontamination agent, at least one super-absorbent polymer, at least one surfactant, and the remainder solvent.

Document [4] describes a biological decontamination gel composed of a colloidal solution comprising at least one inorganic viscosifying agent, generally silica or alumina, an active biological decontamination agent composed of the combination of a mineral base selected from among the hydroxides of alkali metals, the hydroxides of alkaline earth metals and mixtures thereof, with an oxidizing agent stable in a basic medium selected from among permanganates, persulfates, ozone, hypochlorites and mixtures thereof, optionally at least one surfactant and the remainder solvent, the gel not containing any super-absorbent polymer.

In documents [1], [2], [3] and [4], $TiO_2$ is not mentioned among the inorganic viscosifying agents.

The gels in documents [3] and [4], which are gels that can be sprayed and vacuumed, can attack the surface of some metals such as aluminium, in particular on account of the presence of chlorine in their formulation.

These gels show good performance for the removal of toxic biological species, but they have limited chemical stability. As a result, the time during which they can be stored at ambient temperature, whilst maintaining intact their decontamination efficacy, is short.

Indeed, the amount of active chlorine contained in sodium hypochlorite decreases significantly after 6 months if the gel is not stored in a cool place.

There is therefore a need for biological and chemical decontamination gel having long-term efficacy i.e. able to be stored for a long time at ambient temperature, whilst maintaining intact its decontamination efficacy when it is used.

There is a further need for a biological and chemical decontamination gel that ensures efficient surface decontamination and preserves the treated surface i.e. it does not corrode, does not attack and does not deteriorate this surface, in other words it does not cause any chemical, mechanical or physical deterioration of the treated surface.

The objective of the present invention is to provide a decontamination gel which inter alia meets the needs and requirements set forth above.

It is a further objective of the invention to provide a decontamination gel which does not have the disadvantages, defects, limitations and shortcomings of prior art decontamination gels, and which solves the problems of prior art decontamination gels, in particular the gels subject of documents [1], [2], [3], and [4].

DISCLOSURE OF THE INVENTION

This objective and others are reached according to the invention with an adsorbent and photocatalytic decontamination gel, consisting of a colloidal solution comprising, preferably consisting of:

8% to 30% by weight, preferably 10% to 30% by weight, more preferably 15% to 20% by weight, further preferably 15% to 20% by weight the 15% value being excluded, better still 16% to 20% by weight, for example 20% by weight of $TiO_2$, optionally doped, relative to the weight of the gel;

optionally, 0.01% to 10% by weight, preferably 0.1% to 5% by weight relative to the weight of the gel, of at least one dye and/or at least one pigment;

optionally, 0.1% to 2% by weight relative to the weight of the gel of at least one surfactant;

optionally, 0.05% to 5% by weight, preferably 0.05% to 2% by weight relative to the weight of the gel of at least one super-absorbent polymer;

and the balance solvent, said solvent being selected from among mixtures of water and of a C1 to C10 (1 C to 10 C) saturated aliphatic alcohol such as ethanol;

and said gel having a pH of 4 or higher.

By «the balance solvent» is meant that the solvent is always present in the colloidal solution and the amount of solvent is a quantity such that when it is added to the quantities of components of the colloidal solution other than the solvent (whether these components are compulsory or optional components as cited above, or still other optional additional components whether or not cited), the total quantity of all the components of the colloidal solution is 100 weight %.

At all events, the total quantity of all the components of the colloidal solution (whether these components are compulsory or optional as cited above, or still other cited or non-cited optional additional components) is evidently 100 weight %. The gel of the invention is a colloidal solution which means that the gel of the invention contains inorganic solid mineral particles of $TiO_2$, as viscosifying agent, the mean size of the elementary primary particles thereof generally being 2 to 200 nm.

By employing a viscosifying agent that is generally exclusively inorganic, without any organic viscosifying agent, the content of organic matter in the final solid waste obtained after using the gel of the invention is generally less than 4% by weight, preferably less than 2% by weight, which amounts to a further advantage of the gels of the invention.

These inorganic, solid mineral particles act as viscosifier to enable the solution, e.g. the aqueous solution, to gel and therefore adhere to the surfaces of the part to be treated, decontaminated, irrespective of the geometry, shape and size thereof, and irrespective of the location of the contaminants to be removed.

The decontamination gel of the invention can be called a $TiO_2$ based colloidal decontamination gel.

The gel of the invention allows the decontaminating of surfaces contaminated, polluted by all kinds of polluting, contaminating species e.g. ionic, chemical or biological contaminating species.

The gel of the invention differs fundamentally from prior art gels such as those in documents [1], [2], [3] and [4], in that it contains $TiO_2$ as an inorganic viscosifying agent and not silica or alumina.

In other words, in the decontamination gel of the invention the colloidal particles usually used in prior art decontamination gels such as colloidal particles of silica or alumina are replaced by colloidal particles of $TiO_2$.

In addition, the gel of the invention contains an extremely specific amount of $TiO_2$, namely a content of 8% to 30% by weight, preferably 10% to 30% by weight, more preferably 15% to 20% by weight, further preferably 15% to 20% by weight the 15% value being excluded, better still 16% to 20% by weight, for example 20% by weight of $TiO_2$, optionally doped, relative to the weight of the gel.

It has been found, according to the invention that a gel having a $TiO_2$ content, concentration lying within the specific range mentioned above and in particular the 15 to 20% weight range, better still in the 15 to 20 weight % range the 15% value being excluded, and having a pH of 4 or higher, surprisingly has excellent adherence, hold on non-horizontal surfaces such as ceilings or walls.

It is to be noted that the $TiO_2$ is stable over the long term, for example possibly reaching at least one year.

The incorporation of $TiO_2$ in a decontamination gel, in particular in the very specific content mentioned above, in particular in the range of 15% to 20% by weight, better still in the range of 15% to 20% by weight of $TiO_2$, the 15% value being excluded, relative to the weight of the gel, has never been either described or suggested in the prior art and notably in documents [1], [2], [3] and [4] cited above.

The gel of the invention, essentially due to the fact that it contains $TiO_2$ as inorganic viscosifying agent instead of silica or alumina, meets all the needs and requirements indicated above. It does not have the disadvantages, defects, limitations and shortcomings of prior art gels such as the gels in documents [1], [2], [3] and [4] which contain silica or alumina, and not $TiO_2$ as viscosifying agent.

With the gel of the invention it is possible to reach the above-mentioned objectives and to solve the problems of prior art decontamination gels such as those described in documents [1], [2], [3] and [4] without having the disadvantages thereof in particular in terms of surface corrosion, release of contaminating species, low stability and limited storage time, whilst providing high decontamination efficacy irrespective of the contaminating, polluting species.

Surprisingly, in the gel of the invention, titanium dioxide acts not only as inorganic viscosifying agent but also as decontamination agent but with the advantage, compared with the decontamination active agents usually used in prior art decontamination gels such as those in documents [1], [2], [3] and [4], of being fully innocuous for these surfaces and, as already mentioned above, of being stable over long periods.

The gel of the invention therefore has a storage time of at least one year, preferably at least two years, for example from one to two years, i.e. the gel of the invention is stable over this time, it does not undergo any degradation of any kind during this period of time The fact that in the gel of the invention $TiO_2$ acts as active decontamination agent means that the gel of the invention does not comprise any harsh, corrosive active decontamination agents likely to cause deterioration, damage, attack of the surfaces to be treated, such as the active decontamination agents mentioned in documents [1], [2], [3], and [4].

The gel of the invention and also the decontamination method applying this gel (described below) take advantage of the absorbent property and photocatalytic property of titanium dioxide under light radiation to remove the polluting, contaminating species with very high efficacy from the surface of a solid substrate contaminated, polluted with these contaminating species irrespective of type: ionic, chemical, biological, nuclear or radioactive. A detailed description of the contaminating species which can be removed with the method of the invention is given below in the description of the method.

In other words, the gel of the invention has an adsorbent property, adsorbent properties due to $TiO_2$, in particular with regard to ionic contaminating species and contaminating species that are organic chemical compounds, as well as «photocatalytic» properties which for example allow a change in the oxidation state of the ionic compounds or the reduction of organic compounds.

As already indicated above, $TiO_2$ is stable over long periods possibly reaching at least 1 year.

The photocatalytic and adsorbent properties imparted to the gel through the presence of $TiO_2$, and which allow a reduction in the toxicity of the contaminating species, are therefore preserved over long periods of time possibly reaching at least one year contrary to prior art gels.

In other words, one of the remarkable and surprising effects of the gels of the invention is that, since the adsorbent and photoactive properties of the gel derive from $TiO_2$, these properties are maintained over long periods of time, whereas with gels, particularly containing alumina or silica, incorporating decontaminating solutions as active decontamination agents, ageing can lead to loss of efficacy of these decontaminating solutions.

The gel of the invention combines this adsorbent property, power, and this photocatalytic property, power of titanium dioxide, with adequate rheological properties, which inter alia allow the ensured application of the gel via spraying, the adhering thereof on a vertical wall or a ceiling, and allow the dry gel, which is generally in the form of flakes, to be easily removed by brushing or vacuuming, suction, and preferably by vacuuming, suction. The gel of the invention can therefore be qualified a «sprayable gel» and a «vacuumable gel» "sunctionable gel".

It can be said that the presence of titanium dioxide as inorganic, gelling viscosifying agent in the gel of the invention allows the gel of the invention to be sprayable, allows the gel of the invention to be vacuumable after application on the surface to be depolluted, decontaminated, and after drying, and finally allows the gel to have a long storage time.

The terms «vacuumable gel» "suctionable gel" are widely used in this technical field and have a definition that is well-known as recalled above.

The rheological properties of the gel of the invention are due to the rheofluidifying, viscosifying properties of the particles of titanium dioxide dispersed within the solvent of the gel, and to the pH of the gel that is 4 or higher, allowing adjustment of the viscosity of the gel and notably ensuring application of the gel by spraying and the adhering, hold, thereof on a vertical wall or ceiling.

Up until now it had not been evidenced that $TiO_2$ is a viscosifying agent having rheofluidifying properties similar to silica or alumina.

The gels of the invention which contain $TiO_2$ as viscosifying agent thereby surprisingly have the properties of a thixotropic rheofluidifying fluid, the viscosity thereof being able to vary as a function of shear and over time.

In addition, according to the invention, it has been evidenced that from a sufficiently high concentration of $TiO_2$, namely 8 weight %, preferably 10 weight %, more preferably 15 weight %, further preferably more than 15 weight % (the 15% value then being excluded), better still 16 weight % and with an adapted formulation i.e. with a pH of 4 or higher, it is possible to obtain a suspension that is sufficiently stable and viscous, to be able to be called a «gel».

In addition, the $TiO_2$ contained in the gel of the invention as inorganic, mineral viscosifier, has an unexpected impact on the drying of the gel of the invention and on the particle size of the residue obtained.

Indeed, the dry gel is in the form of particles of controlled size, more specifically of millimetric solid flakes having a mean size generally ranging from 1 to 10 mm, preferably 2 to 5 mm, in particular due to the fact that the inorganic viscosifying agent consists of $TiO_2$.

It is specified that the size of the particles, such as flakes, generally corresponds to their largest dimension.

In other words, the solid mineral particles of $TiO_2$ in the gel of the invention, in addition to their viscosifying role, also play a fundamental role upon drying of the gel since they ensure fracturing of the gel leading to a dry waste in flake form.

More exactly, when preparing the gel, the $TiO_2$ particles are initially dispersed within the solvent which according to the invention is a hydroalcoholic solvent, and the pH is increased to a value of 4 or higher to adjust the viscosity of the system thus enabling the spraying and then hold, adhering thereof on the surface to be decontaminated, in particular on a vertical wall or ceiling.

The pH of the gel can also be adjusted so that there is no or only scarce chemical attack of the surface during treatment i.e. the pH is then adjusted so that the gel is slightly acidic or slightly basic, even neutral.

Indeed, one of the advantages of the gel of the invention is that it is possible to vary easily the pH thereof.

Therefore, if it is desired not to attack the surface, the pH can be adapted to the surface to be decontaminated.

On the other hand, if slight surface attack is desired, the pH of the gel can be modified to allow this attack.

Or else the pH of the gel can be adjusted so that the gel is strongly basic e.g. 9 or higher to impart a degreasing property, power, to the gel.

Irrespective of the pH of the gel of the invention, the surface treated with the gel of the invention is decontaminated and can optionally be degreased, and at all events it remains intact, it is not attacked, corroded. This surface can therefore optionally be reused after decontamination.

According to the invention, it is therefore possible to formulate a neutral, basic or weak acidic gel which combines the adsorbent property and photocatalytic property of titanium dioxide under light radiation, with rheological properties particularly allowing the gel to be sprayable and vacuumable.

Indeed, titanium dioxide has excellent adsorbing properties of ions and organic chemical compounds.

More specifically, the sorption of water on the surface of titanium dioxide causes the formation of hydroxyl groups OH which are preferred sites for the sorption of ions via surface complexing mechanisms.

Titanium dioxide is therefore capable of capturing a large number of ions on its surface.

The gel of the invention, based on $TiO_2$, uses this property to adsorb ions, this ion-adsorbing property, and hence ion extraction property of $TiO_2$, to improve the capturing of contaminating ionic species present on a surface to be decontaminated, but without chemically attacking the surface.

Similarly, the gel of the invention containing $TiO_2$, uses this property to adsorb organic chemical compounds, this adsorbing property of organic chemical compounds, and hence this property of extraction of organic chemical compounds that $TiO_2$ has, to improve the capturing of contaminating species which are organic chemical compounds present on a surface to be decontaminated, but without chemically attacking the surface.

In addition, after treatment, the contaminating, polluting species contained in the gel flakes remain chemically bonded to the $TiO_2$ and thereby ensure the confining of this pollution and hence minimizing the risk of disseminating the pollution in the environment in the event of accidental leaching of the dry gel flakes.

In other words, by means of the adsorption property, power, of $TiO_2$, which allows adsorption on its surface of contaminating, polluting species especially of ionic species, the extracted contaminating species, especially the ionic species, are chemically bonded on the flakes, therefore limiting any release into water should it happen to leach the dry gel flakes during storage of the gel.

In addition, titanium dioxide has a very strong photocatalytic property, power.

Titanium dioxide is highly active and allows the photochemical reduction of numerous contaminating, polluting species and in particular of hexavalent chromium to trivalent chromium.

In the event of a pollution, contamination with a contaminating species that is a multivalent element in ionic form, such as chromium Cr, or a heavy metal such as arsenic As or mercury Hg, a change in the oxidation state of the contaminating species can lead to a drastic decrease in the toxicity thereof.

The rate of reduction of hexavalent chromium is especially strongly increased with acid gels (generally of pH<6: the gel therefore has a pH of 4 to 6) and under the action of a UV radiation.

To summarize, the photocatalytic property of the gel due to $TiO_2$, allows a reduction in the oxidation state of ionic pollutants thereby generating a drop in their toxicity (the case with Cr(VI) in the different examples).

Therefore, the gel of the invention meets a very large existing need which was not met by prior art gels.

It has also been shown (see below and examples) that the addition of an alcohol such as ethanol allows an improvement in the reducing efficacy of the gel of the invention, for example the reduction rate of hexavalent chromium by acting within the system as inhibitor of the recombining of electron-hole pairs, thereby making easier the capture of an electron by chromium (VI) and hence its reduction.

The photocatalytic nature of $TiO_2$ also allows the destruction of chemical and biological pollutants.

Indeed, under the action of a UV radiation, hydroxyl radicals are formed by oxidation of the water adsorbed on the surface of the $TiO_2$.

These radicals react with the chemical or biological pollutants degrading them and thereby annihilating their toxicity.

It can be said that the gel of the invention, by means of a mixed phenomenon of adsorption of the contaminant within the gel phase and of photocatalytic property, power, of $TiO_2$, has a triple property, power, triple action, namely:
- the property, power, action of removing contaminating, polluting species;
- the property, power, of binding the contaminating, polluting species within the dry gel flakes;
- the property, power, of reducing the toxicity of the contaminating, polluting species, irrespective of these polluting, contaminating species whether they are ionic, chemical or biological polluting, contaminating species for example.

It is additionally noted, on account of the chemical stability of $TiO_2$ in the specific solvent of the gel of the invention, which is a hydroalcoholic solvent, that the gel of the invention can be preserved, stored for a very long period of time possibly reaching one year for example and even two years, or longer.

To conclude, the gel of the invention allows very simple decontamination of surfaces polluted with ionic contaminating species, but also with chemical, biological, radioactive or nuclear contaminating species, through the combination of the adsorption efficacy and of the photocatalytic properties of titanium dioxide under light radiation.

Also, the gel of the invention has the man known advantages of decontamination gels, namely: low cost, ease of use in particular by spraying, and ease of management of the final waste which is generally in the form of vacuumable, suctionable flakes, without the production of liquid effluents.

In addition, the formulation of the gel does not contain any harsh active decontamination agent for the surfaces to be treated.

Another fundamental characteristic of the gel of the invention is that it contains a very specific solvent selected from among mixtures of water and of a saturated C1 to C10 aliphatic alcohol such as ethanol.

As already indicated above, it has been shown (see examples) that the addition of an alcohol such as ethanol to the gel allows to improve the reducing efficacy, efficiency, of the gel, for example the reduction rate of hexavalent chromium, by acting within the system as inhibitor of the recombination of electron-hole pairs, thereby making easier the capture of an electron by chromium (VI) and hence the reduction thereof.

In addition, it has surprisingly been evidenced that the presence of an alcohol such as ethanol in the gel of the invention (see examples) allows an increase in the flow threshold of the gel compared with an aqueous gel having a solvent consisting solely of water. This therefore allows a greater thickness of gel to be deposited on non-horizontal surfaces such as walls or ceilings.

In other words, the presence of an alcohol such as ethanol in the gel of the invention allows a further improvement in the adhering, hold, of the gel onto surfaces that are not horizontal such as ceilings or walls (see examples) compared with an aqueous gel having a solvent consisting solely of water.

As already indicated above, the gel of the invention may have a slightly acidic pH of 4 (inclusive of 4) to less than 7 (i.e. 4 to 7, 7 being excluded); a neutral pH of 7; or a slightly basic pH of more than 7 to less than 9; or a very basic pH of 9 or higher One preferred pH is 5 (inclusive) to 9 (inclusive).

Particularly preferred pH values are 5, 5.5 and 9.

Irrespective of the pH of the gel of the invention, no corrosion, attack, deterioration, aggression of the treated surface is generally observed, and this surface remains intact.

Advantageously, the pH is adjusted by the addition of a mineral base.

This mineral base may be selected for example from among sodium hydroxide NaOH, potassium hydroxide KOH, and mixtures thereof.

This mineral base generally does not act as decontamination agent as in the prior art methods.

However, it may only and optionally impart degreasing properties to the gel when the pH of the gel is 9 or higher, and if contaminants are contained in the grease, in which case it could optionally be considered that this base does act as decontamination agent, the $TiO_2$ then acting as adsorbent of contaminants such as radionuclides contained in the grease.

The concentration of the mineral base in the gel is the concentration required to adjust the pH of the gel to the desired value, of 4 or higher and advantageously between 5 and 9.

Advantageously, the concentration of the mineral base may range from $1 \cdot 10^{-3}$ M to $2 \cdot 10^{-2}$ mol/L of gel.

Said concentration does not enable this inorganic base to act as contaminating agent and does not lead to any corrosion, deterioration, attack of the surface to be decontaminated.

Said concentration is low and can generally be neglected in relation to the weight of solvent and weight of $TiO_2$ in the gel.

The gel of the invention may further, optionally, contain at least one dye and/or at least one pigment.

Advantageously, the pigment is a mineral pigment. In this respect, reference may be made to document WO-A1-2014/154817.

There is no limitation as to the mineral pigment that can be incorporated in the decontamination gel of the invention.

In general, the mineral pigment is selected from among mineral pigments that are stable in the gel.

By stable pigment, it is generally meant that the pigment does not exhibit any stable change in colour over time, when the gel is stored for a minimum time of 6 months.

There is no limitation as to the colour of this pigment, which is generally the colour it will impart to the gel. This colour of the pigment can be black, red, blue, green, yellow, orange, purple, brown, etc. and even white.

In general, the gel therefore has the same colour as the colour of the pigment it contains. However, it is possible that the gel has a colour differing from the colour of the pigment it contains, but this is not sought after.

The pigment, in particular when it is white, generally differs from the inorganic viscosifying agent Advantageously, the mineral pigment is selected so that it imparts the gel (i.e. the gel in the wet state before drying) with a colour differing from the colour of a surface to be decontaminated onto which the gel is applied.

Advantageously, the mineral pigment is a micronized pigment and the mean size of the mineral pigment particles can range from 0.05 to 5 µm, preferably from 0.1 to 1 µm.

By micronizing the pigment, it can be prevented from modifying the rheology and spraying ability of the gel («sprayability») since the pigment then has the same micrometric size that is generally the size of the inorganic viscosifying agent, such as aggregates of alumina.

Advantageously, the mineral pigment is selected from among metal(s) and/or metalloid(s) oxides, metal(s) and/or metalloid(s) hydroxides, metal(s) and/or metalloid(s) oxyhydroxides, metal(s) ferrocyanides and ferricyanides, metal(s) aluminates, and mixtures thereof.

Preferably, the mineral pigment is selected from among iron oxides, preferably micronized, and mixtures thereof.

Iron oxides can have different colours and for example can be yellow, red, purple, orange, brown or black.

Indeed, iron oxide pigments are known to have a good covering power and strong resistance to acids and bases.

For incorporation in a decontamination gel, iron oxides show better performance in terms of stability and colouring power. For example, an iron oxide content of 0.1%, even 0.01% by weight is sufficient to obtain strong colouring of the gel without modifying the properties thereof.

As already indicated above, the fact that the iron oxide pigment is preferably micronized, means that it can be prevented from modifying the rheology and spray capability of the gel («sprayability») since the pigment is then of micrometric size, namely a size generally that of the inorganic viscosifying agent, such as aggregates of alumina.

Micronized iron oxides are available from Rockwood® under the trade name Ferroxide®.

Mention can be made inter alia of Ferroxide® 212 M which is a micronized red iron oxide with a mean particle size of 0.1 µm, and Ferroxide® 228 M which is micronized red iron oxide with a mean particle size of 0.5 µm.

In addition to and/or instead of iron oxides, other coloured oxides or hydroxides of metals or metalloids may be incorporated in the gel of the invention, as a function of the pH of the gel, particular mention being made of vanadium oxide ($V_2O_5$) which is orange, manganese oxide ($MnO_2$) which is black, cobalt oxide which is blue or green, and the oxides of rare earths. However, iron oxides are preferred for the reasons set forth above.

Among oxyhydroxides, mention may be made of goethite, i.e. iron oxyhydroxide FeOOH, which is highly coloured.

As an example of metal ferrocyanide, Prussian blue may be cited i.e. ferric ferrocyanide, and as aluminate cobalt blue may be cited, i.e. cobalt aluminate.

The incorporation in the gel of the invention of mineral pigment allows better visualization of the wet gel and of the dry residues irrespective of the substrate onto which the gel is applied.

The gel of the invention may optionally also contain at least one super-absorbent polymer.

By «super-absorbent polymer» also known as «SAP», it is generally meant a polymer in the dry state capable of spontaneously absorbing at least 10 times, preferably at least 20 times of a weight aqueous liquid, especially water, and particularly distilled water.

Some «SAPs» are able to absorb up to and even more than 1000 times their weight of liquid.

Said super-absorbent polymers are notably described in the work «*Absorbent Polymer Technology, Studies in Polymer Science 8*» by L. BRANNON-PAPPAS and R. HARLAND, Elsevier publications, 1990, to which reference may be made.

By spontaneous absorption it is meant an absorption time ranging up to about one hour.

The super-absorbent polymer may have a water absorption capacity of 10 to 2000 times its own weight, preferably 20 to 2000 times its own weight (i.e. 20 g to 2000 g of water absorbed per gram of absorbent polymer), more preferably 30 to 1500 times, and in particular 50 to 1000 times.

These water absorption characteristics relate to normal conditions of temperature (25° C.) and pressure (760 mm Hg i.e. 100000 Pa) and for distilled water.

The SAP optionally contained in the decontamination gel of the invention may be selected from among sodium poly(meth)acrylates, starches grafted with a (meth)acrylic polymer, hydrolysed starches grafted with a (meth)acrylic polymer; polymers based on starch, gum, and a cellulose derivatives; and mixtures thereof.

More specifically, the SAP that can optionally be used in the gel of the invention can be selected for example from among:
- polymers resulting from polymerisation with partial crosslinking of water-soluble ethylenically unsaturated monomers such as acrylic, methacrylic polymers (particularly derived from polymerisation of acrylic and/or methacrylic acid and/or of acrylate and/or methacrylate monomers), or vinyl polymers in particular crosslinked and neutralised poly(meth)acrylates notably in gel form; and the salts in particular the alkaline salts such as the sodium or potassium salts of these polymers;
- starches grafted with polyacrylates;
- acrylamide/acrylic acid copolymers, particular in the form of sodium or potassium salts;
- starches grafted with acrylamide/acrylic acid, in particular in the form of sodium or potassium salts;
- the sodium or potassium salts of carboxymethylcellulose;
- the salts particularly the alkaline salts of crosslinked polyaspartic acids;
- the salts particularly the alkaline salts of crosslinked polyglutamic acids.

In particular, as «SAP», a compound can be used selected from among:
- crosslinked sodium or potassium polyacrylates sold under the trade names SALSORB CL 10, SALSORB CL 20, FSA type 101, FSA type 102 (Allied Colloids); ARASORB S-310 (Arakawa Chemical); ASAP 2000, Aridall 1460 (Chemdal); KI-GEL 201-K (Siber Hegner); AQUALIC CA W3, AQUALIC CA W7, AQUALIC CA W10; (Nippon Shokuba); AQUA KEEP D 50, AQUA KEEP D 60, AQUA KEEP D 65, AQUA KEEP S 30, AQUA KEEP S 35, AQUA KEEP S 45, AQUA KEEP Al M1, AQUA KEEP Al M3, AQUA KEEP HP 200, NORSOCRYL S 35, NORSOCRYL FX 007 (Arkema); AQUA KEEP 10SH-NF, AQUA KEEP J-550 (Kobo); LUQUASORB CF, LUQUASORB MA 1110, LUQUASORB MR 1600, HYSORB C3746-5 (BASF); COVAGEL (Sensient technologies), SANWET IM-5000D (Hoechst Celanese);
- starch-grafted polyacrylates sold under the trade names SANWET IM-100, SANWET IM-3900, SANWET IM-50005 (Hoechst);
- starch-grafted acrylamide/acrylic acid copolymers in the form of sodium or potassium salt, sold under the trade names WATERLOCK A-100, WATERLOCK A-200, WATERLOCK C-200, WATERLOCK D-200, WATERLOCK B-204 (Grain Processing Corporation);
- acrylamide/acrylic acid copolymers in sodium salt form, sold under the trade name WATERLOCK G-400 (Grain Processing Corporation);
- carboxymethylcellulose sold under the trade name AQUASORB A250 (Aqualon);
- crosslinked sodium polyglutamate sold under the trade name GELPROTEIN (Idemitsu Technofine).

Super-absorbent polymers, in particular super-absorbent polymers (polyelectrolytes) containing alkaline ions such as sodium or potassium ions, e.g. of sodium or potassium poly(meth)acrylate type, impart numerous properties to the decontamination gels of the invention.

They first impact the rheology of the product, in particular the flow threshold thereof. In terms of implementation of the method, the advantage of super-absorbent polymers is to guarantee perfect adherence of the gel onto the treated materials, in particular on vertical and overhanging surfaces when the thickness of the sprayed gel is greater than 1 mm.

In a decontamination method using a gel, a super-absorbent polymer is of particular advantage since, via hydrogen bonding, it absorbs part of the solution contained in the gel. The number of hydrogen bonds formed between the gel solution and the super-absorbent polymer such as sodium polyacrylate being a function of the salt load, phenomena of absorption/desorption occur when the salt load of the decontamination gel is modified.

This mechanism is therefore of particular advantage when mineral porous materials are to be decontaminated, such as cementitious matrices for example.

When in contact with the material, the salt load of the gel is increased on account of the presence of mineral particles that very often contain calcium. Within the super-absorbent polymer such as sodium polyacrylate, the substitution of the $Na^+$ counter-ion by $Ca^{2+}$ derived from the calcium instantly generates a phenomenon of release of solution, for example of biocidal solution, on account of the higher steric hindrance of the calcium ion.

The quantity of solution released by the super-absorbent polymer such as sodium polyacrylate is then able to diffuse immediately into the porosity of the material and penetrate at depth.

The diffusing phenomenon of the decontamination agent towards the core of the material is much more limited for a gel not containing any super-absorbent.

The adding of super-absorbent polymer to the gel of the invention therefore allows a significant increase in the efficacy of the gel, and of the method of the invention, in the presence of porous materials contaminated at depth over a thickness of one or more millimetres, for example up to 2, 5, 10, 20 even 100 mm.

The super-absorbent polymer is preferably selected from among the Aquakeep® or Norsocryl® ranges marketed by ARKEMA.

The gel may optionally and additionally contain at least one surfactant (namely a single surfactant or a mixture of surfactants), preferably this or these surfactant(s) like being selected from the family of non-ionic surfactants such as block copolymers, block copolymers of ethylene oxide and propylene oxide, and ethoxylated fatty acids; and mixtures thereof.

For this type of gel, the surfactants are preferably block copolymers marketed by BASF under the trade name PLURONIC®.

Pluronics® are block copolymers of ethylene oxide and propylene oxide.

These surfactants impact the rheological properties of the gel, in particular the thixotropic nature of the product and its recovery, reset time, and prevent the onset of run-off.

Surfactants additionally provide control over the adherence of the dry waste, and control over the size of the flakes of dry residue to guarantee the non-powdery nature of the waste.

Preferably, the solvent is selected from among mixtures of water in a proportion of 10% to 80% by weight, preferably 40% to 70% by weight, more preferably 40% to 56% by weight, e.g. 40%, 42.5%, or 56% by weight, and of a saturated C1 to C10 aliphatic alcohol such as ethanol in a proportion of 10% to 60% by weight, preferably 10% to 50% by weight, more preferably 24% to 42.5% by weight, further preferably 24% to 40% by weight, e.g. 24%, 40%, or 42.5% by weight relative to the weight of the gel.

The quantity of water and the quantity of saturated aliphatic alcohol such as ethanol are such that, when added to the quantities of constituents of the colloidal solution other than the solvent (whether these constituents are compulsory or optional as cited above, or other optional cited or non-cited additional constituents), the total quantity of all the constituents of the colloidal solution is 100% by weight.

One particularly preferred gel of the invention comprises 42.5 weight % water and 42.5 weight % of a saturated C1 to C10 aliphatic alcohol, such as ethanol, and 15 weight % $TiO_2$ relative to the weight of the gel. The pH of this gel may be from 5.5 to 9, for example 5.5 or 9.

Another particularly preferred gel of the invention comprises 56 weight % water, 24 weight % of a saturated C1 to C10 aliphatic alcohol such as ethanol, and 20 weight % $TiO_2$ relative to the weight of the gel. The pH of this gel may be 5.

A further particularly preferred gel of the invention comprises 40 weight % water, 40 weight % of a saturated C1 to C10 aliphatic alcohol such as ethanol, and 20 weight % $TiO_2$ relative to the weight of the gel. The pH of this gel may be 5.

As already mentioned, it has surprisingly been shown that the addition of an alcohol such as ethanol to the gel also allows an improvement in the reducing efficacy of the gel e.g. the rate of reduction of hexavalent chromium.

The invention further concerns a method for decontaminating at least one surface of a substrate made of a solid material, said surface being contaminated by at least one contaminating species on said surface and (optionally) possibly below (underneath) said surface (in the subsurface) in the depth of the substrate, wherein at least one cycle is performed comprising the following successive steps:

a) applying the gel of the invention such as described above on said surface;

b) maintaining the gel on the surface at least for a sufficient time for the gel to absorb the contaminating species, and then for the contaminating species to be adsorbed on the surface of the $TiO_2$, particles, and for the gel to dry and form a dry and solid residue containing said contaminating species adsorbed on the surface of the $TiO_2$ particles;

c) removing the dry and solid residue containing said contaminating species adsorbed in the gel on the surface of the $TiO_2$ particles.

When the contaminating species is on the surface, the term contamination on the surface or surface contamination is used, and hence the term decontamination of/on the surface or surface decontamination.

When the contaminating species is below (underneath) said surface, in the depth of the substrate, the term contamination of/in the subsurface or subsurface contamination is used, and hence the term decontamination of/in the subsurface or subsurface decontamination.

The method of the invention allows subsurface decontamination of porous materials (Example 4).

However, the method of the invention does not allow decontamination at great depth but only over a depth possibly reaching a few microns, generally over a depth of possibly up to 5 microns from the surface of the substrate, and advantageously over a depth of up to 2 microns from the surface of the substrate.

It is to be noted that in the case of a non-porous surface, the «inactivated» contamination, for example the biological contamination, which is solely a surface contamination, is recovered by the flakes of dry gel.

On the other hand, for deep contamination as is the case with porous materials such as cementitious matrices, the dry gel will contain the residue of surface contamination and the residue of subsurface contamination (contamination residue found up to a few microns from the surface).

The solid substrate may be a porous substrate, preferably a mineral porous substrate. However, the efficacy of the gel and of the method of the invention is just as good in the presence of a non-porous and/or non-mineral surface.

Advantageously, the substrate is made of at least one solid material selected from among metals and metal alloys like stainless steel, painted steels, aluminium and lead; polymers such as plastic materials or rubbers like poly(vinyl chloride)s or PVC, polypropylenes or PP, polyethylenes or PE, in particular high density polyethylenes or HDPE, poly(methyl methacrylate)s or PMMA, poly(vinylidene fluoride)s or PVDF, polycarbonates or PC; glasses; cements and cement materials; mortars and concretes; plasters; bricks; natural or artificial stone; ceramics.

The contaminating species may particularly be selected from among ionic, chemical, biological, nuclear or radioactive contaminating species.

The gel and the method of the invention allow the removal of the contaminating species irrespective of species whether organic or mineral, liquid or solid; or irrespective of the form of this contaminating specie: whether this contaminant is in solid or particulate form, contained in a surface layer of the material of the part, in the form of a film or contained in a film e.g. a film of grease on the surface of the part, or just simply deposited on the surface of the part.

Depending on the type of contamination, the mode of action of the gel of the invention differs: solubilisation of the contaminating film e.g. of grease (with a basic gel for example) or adsorption followed by inactivation and/or degradation, and/or reduction, and/or destruction (via photocatalysis) in situ of the contaminants, particularly chemical or biological if they are pathogenic species (anthrax).

By ionic decontamination gel is meant any gel which, when placed in contact with an ionic species and in particular a toxic ionic species, is able to extract this species and reduce the toxicity thereof. This reduction of toxicity generally takes place by reduction of the ionic species.

This ionic species can be selected from among monovalent and multivalent metal ions, in particular from among toxic monovalent and multivalent metal ions such as ions of chromium (VI), nickel (II), silver (I), cadmium (II), mercury (II), arsenic (III) and lead (II).

The method of the invention, using the gel of the invention, can therefore be applied to decontaminate a smooth surface contaminated with polluting ions. These polluting ions are removed from the surface by absorption within the gel, without chemical attack of the surface, followed by adsorption on the surface of the $TiO_2$ particles.

The method of the invention, using the gel of the invention, can therefore be applied to decontaminate a porous surface contaminated with polluting ions. These polluting ions are removed from the surface via absorption within the gel, without chemical attack of the surface, followed by adsorption on the surface of the $TiO_2$ particles.

By biological decontamination gel, that can also be termed a biocidal gel, is meant any gel which, when placed in contact with a biological species and in particular a toxic biological species, is able to inactivate or destroy the latter, or reduce the toxicity thereof.

By biological species is meant any type of microorganism such as bacteria, fungi, yeasts, viruses, toxins, spores in particular spores of Bacillus anthracis, prions, and protozoa.

The biological species that are removed, destroyed, inactivated by the gel of the invention are essentially biotoxic species such as pathogenic spores e.g. spores of *Bacillus anthracis*, toxins e.g. the botulinum toxin or ricin, bacteria e.g. the *Yersinia pestis* bacteria and viruses e.g. the vaccine virus or viruses of haemorrhagic fevers e.g. of Ebola type.

By chemical decontamination gel is meant any gel which, when placed in contact with a chemical species and in particular a toxic chemical species, is able to destroy or inactivate the latter or reduce the toxicity thereof. This chemical species is generally an organic molecule.

The chemical species removed by the gel of the invention are particularly toxic chemical species such as toxic gases, in particular neurotoxic or blistering.

These toxic gases are particularly organophosphorus compounds among which mention can be made of Sarin or agent GB, VX, Tabun or agent GA, Soman, Cyclosarin, diisopropyl fluorophosphonate (DFP), Amiton or agent VG, Parathion. Other toxic gases are mustard gas or agent H or agent HD, Lewisite or agent L, agent T.

The nuclear, radioactive agents that can be removed with the gel of the invention may be selected for example from among metal oxides and hydroxides, in particular in the form of solid precipitates.

It is to be noted that with regard to radioactive species, we do not talk about the destruction or inactivation but only about the transfer of the nuclear contamination, ionic or in solid form towards the dry gel flakes.

Advantageously, the gel is applied to the surface to be decontaminated in a proportion of 100 g to 2000 g of gel per $m^2$ of surface area, preferably 500 to 1500 g of gel per $m^2$ of surface area, more preferably 600 to 1000 g of gel per $m^2$ of surface area, which generally corresponds to a thickness of gel deposited on the surface of 0.1 mm to 2 mm, preferably 0.5 mm to 2 mm, more preferably 1 mm to 2 mm.

Advantageously, the gel is applied to the solid surface by spraying, using a brush or float.

Advantageously during all or part of step a), and/or during all or part of step b), preferably during the entire duration of step b), the gel maintained on the surface is exposed to a visible radiation or to a A, B or C Ultraviolet radiation (UVA, UVB or UVC), or to another radiation, so as to inactivate and/or degrade and/or reduce and/or destroy the contaminating species by photocatalysis.

Exposure of the gel to a radiation other than the visible radiation or a A, B or C Ultraviolet radiation could be envisaged in particular if the $TiO_2$ is doped with a suitable chemical element.

It is possible to expose the gel to a radiation (to irradiate the gel) only during a part of step b) which would allow modulation of the photocatalytic effect. The photocatalytic effect only takes place during the time of irradiation.

By exposing the gel deposited on the surface to a visible radiation, and preferably to an ultraviolet radiation, or to another radiation, advantage is taken of the photocatalytic effect of the $TiO_2$ contained in the gel of the invention to achieve decontamination, for example to reduce ions or to degrade chemical contaminating species such as organic molecules, or biological contaminating species.

The dry residue has lesser toxicity than the initial pollution, contamination, in the event of pollution caused by a reducible ionic contaminating species such as a multivalent ion.

The contaminating species is reduced under radiation, due to the photocatalytic effect of the $TiO_2$ particles constituting the dry gel flakes, to a reduced species having an oxidation state such that the toxicity of the reduced species is less than that of the initial contaminating species.

Similarly, the dry residue has lesser toxicity than the initial pollution, contamination in the event of pollution caused by a chemical contaminating species such as an organic molecule.

Indeed, the contaminating species is oxidized under radiation, due to the photocatalytic effect of the $TiO_2$ particles constituting the dry gel flakes, to one or more molecules having lesser toxicity than the initial contaminating species.

Also similarly, the dry residue has lesser toxicity than the initial pollution, contamination in the event of pollution caused by a biological contaminating species such as a microorganism.

Indeed, the microorganism is inactivated under radiation, due to the photocatalytic effect of the $TiO_2$ particles constituting the dry gel flakes, to a biological product having lesser toxicity than the initial contaminating species.

In other words, and in general, the photocatalytic properties of the gel allow activation at will of the degradation/reduction of the toxicity of the contaminating species.

Advantageously (during step b)), drying is conducted at a temperature of 1° C. to 50° C., preferably 15° C. to 25° C., under relative humidity of 20% to 80%, preferably 20% to 70%.

Advantageously the gel is maintained on the surface for a time of 2 to 72 hours, preferably 2 to 48 hours, more preferably 4 to 24 hours.

Advantageously, the dry solid residue is in the form of particles, e.g. flakes, having a size of 1 to 10 mm, preferably 2 to 5 mm.

Advantageously, the dry solid residue is removed from the solid surface by brushing and/or vacuuming, suction.

According to the invention, the residue of dry gel containing the contaminating species confines this contaminating species, in particular if it is an ionic contaminating species, by means of chemical complexing via adsorption of the ions on the surface of the constituent $TiO_2$ particles of the dry gel residue, in general flakes of dry gel. By means of this adsorption of the contaminating species, there is no release of the contaminating species, particular of the ionic species, in the event of leaching of the dry gel residue, especially in the form of flakes.

Advantageously, the above-described cycle may be repeated 1 to 10 times using the same gel during all the cycles or using different gels during one or more cycle(s).

Advantageously, during step b), before total drying, the gel is rewetted with a solvent, preferably with the solvent of the gel applied at step a), which in generally avoids repeating application of the gel to the surface and entails savings of reagent and a limited amount of waste. This rewetting operation may be repeated 1 to 10 times for example.

The method of the invention has all the advantageous properties inherent in the decontamination gel used, essentially due to the $TiO_2$ content of the gel, these having been largely set forth above.

To summarise, the method and gel of the invention particularly have the following advantageous properties:
- application of the gel by spraying;
- adherence to walls and ceilings;
- obtaining of maximum decontamination efficacy at the end of the drying phase of the gel, including in situations of penetrating contamination particularly in the case of porous surfaces (subsurface decontamination: see above).

In general, it is provided that the drying time is equal to or longer than the time needed for adsorption and optionally inactivation and/or degradation and/or reduction and/or destruction of the contaminating species by photocatalysis by exposure to a radiation.

In the event of in-depth adsorption and optionally inactivation, recourse is generally made to rewetting.

In other words, if the contaminating species must undergo photocatalytic treatment to reduce the toxicity thereof, it is provided that the drying time is equal to or longer than the time needed for adsorption and photocatalytic inactivation of the contaminating species.

Otherwise, if photocatalytic treatment of the contaminating species is not necessary, then to reduce the toxicity thereof it is sufficient to provide a drying time that it simply equal to or longer than the time needed for adsorption.
- treatment of a very wide range of materials;
- no mechanical or physical deterioration of the materials at the end of the treatment;
- implementation of the method under variable weather conditions;
- reduction in the volume of waste;
- easy recovery of the dry waste.

Other characteristics and advantages of the invention will become better apparent on reading the following detailed description given for illustrative and non-limiting purposes, with reference to the appended drawings.

This graph is called «$TiO_2$—$H_2O$ gel in the dark».

The wavelength is given along the X-axis (in nm), and the absorbance along the Y-axis.

Figure 2:
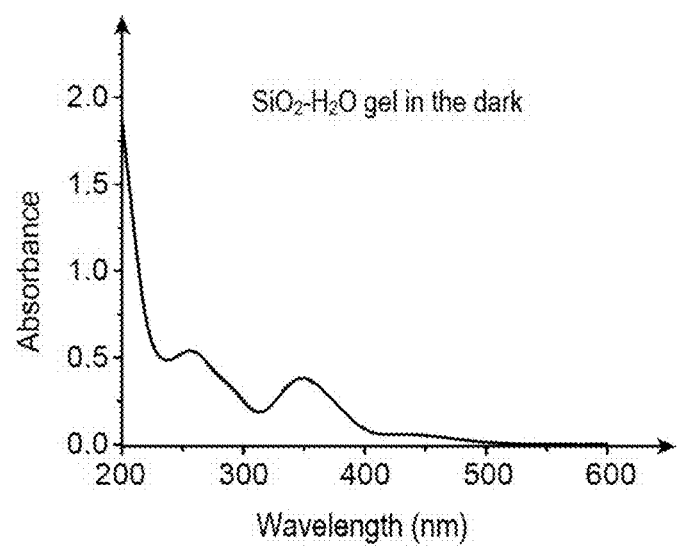

FIG. 2 is a graph illustrating the UV-Visible spectrum of the solution obtained in Example 3 after leaching of the flakes of a comparative gel not conforming to the invention, containing $SiO_2$, namely the gel prepared in Example 3 for which the solvent is water and which was applied and dried in the dark.

This graph is called «$SiO_2$—$H_2O$ gel in the dark».

The wavelength is given along the X-axis (in nm), and the absorbance along the Y-axis.

Figure 3:
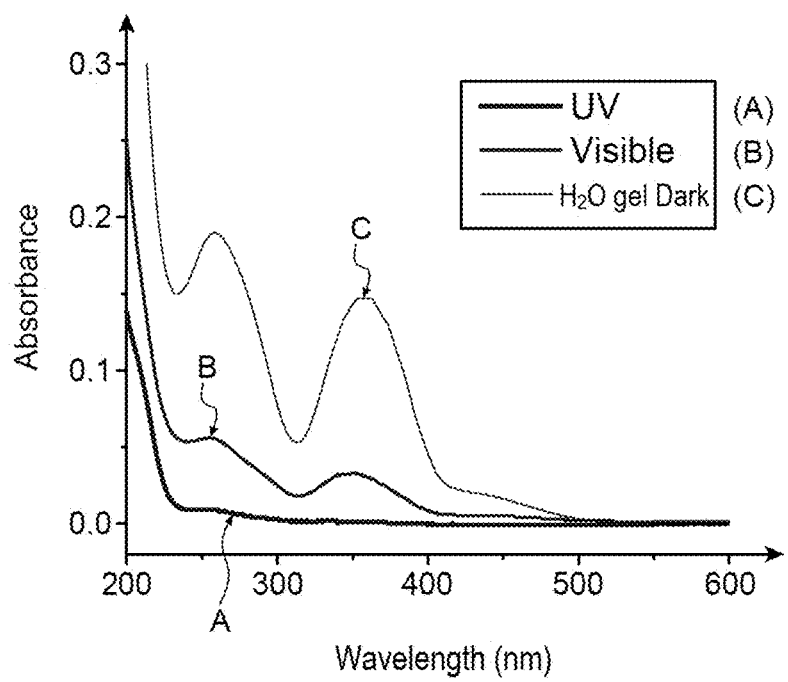

FIG. 3 is a graph illustrating the UV-Visible spectrum of the solutions obtained after leaching of the flakes of the gel («$H_2O$-40 EtOH gel») according to the invention described in Example 5.

These flakes were obtained either by drying under the radiation of an UV lamp (Curve A) or by drying under visible light (Curve B).

For comparison, this graph also shows the UV-Visible spectrum (curve C) of the solution obtained after leaching of the flakes of a $TiO_2$ gel, namely the gel prepared in Example 1 the solvent of which is water and which was applied and dried in the dark.

The wavelength is given along the X-axis (in nm), and the absorbance along the Y-axis.

Figure 4:
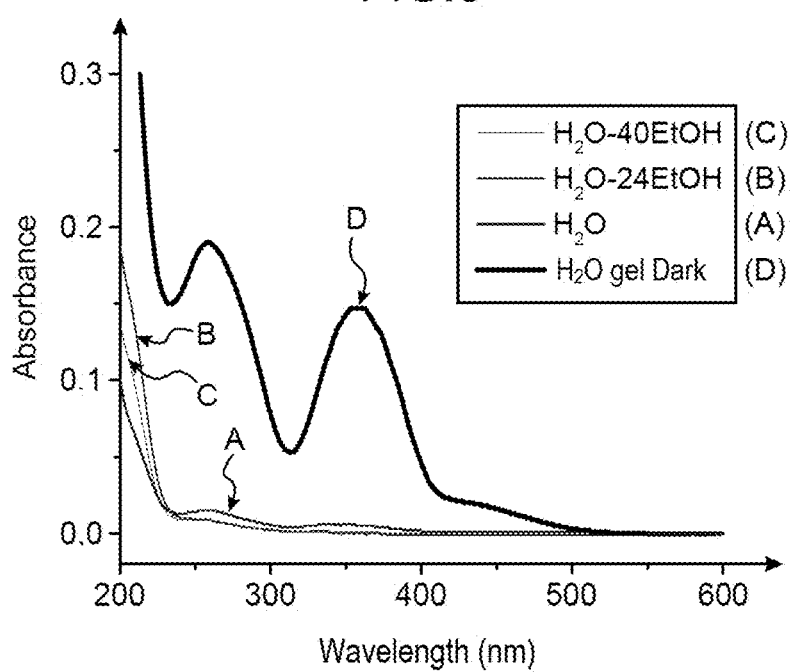

FIG. 4 is a graph illustrating the UV-Visible spectrum of the solutions obtained after leaching of flakes of the gel («$H_2O$ gel» (Curve A), «$H_2O$-24 EtOH gel» (Curve B), and «$H_2O$-40 EtOH gel» (Curve C)) described in Example 7 (see Table 7).

These flakes were obtained by drying under an UV lamp.

For comparison, this graph also shows the UV-Visible spectrum (Curve D) of the solution obtained after leaching of the flakes of a $TiO_2$ based gel of the invention, namely the gel prepared in Example 1, for which the solvent is water and which was applied and dried in the dark.

The wavelength is given along the X-axis (in nm), and the absorbance along the Y-axis.

Figure 5:
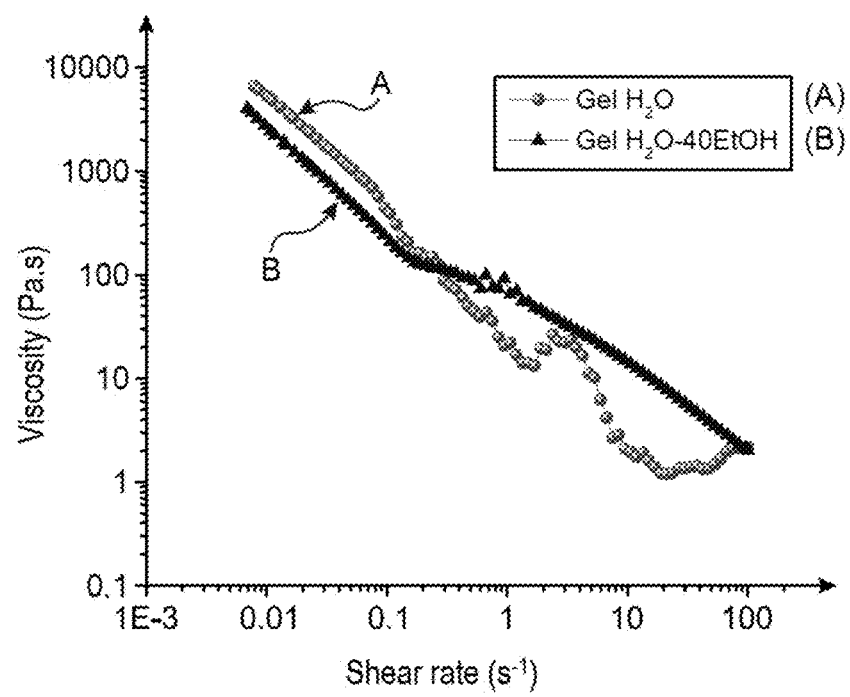

FIG. 5 is a graph illustrating the change in viscosity as a function of shear rate of the «$H_2O$ gel» (Curve A) and of the «$H_2O$-40EtOH gel» (Curve B) (see Example 8).

The shear rate is given along the X-axis (in s−1) and the viscosity is given along the Y-axis (in Pa·s).

Figure 6:
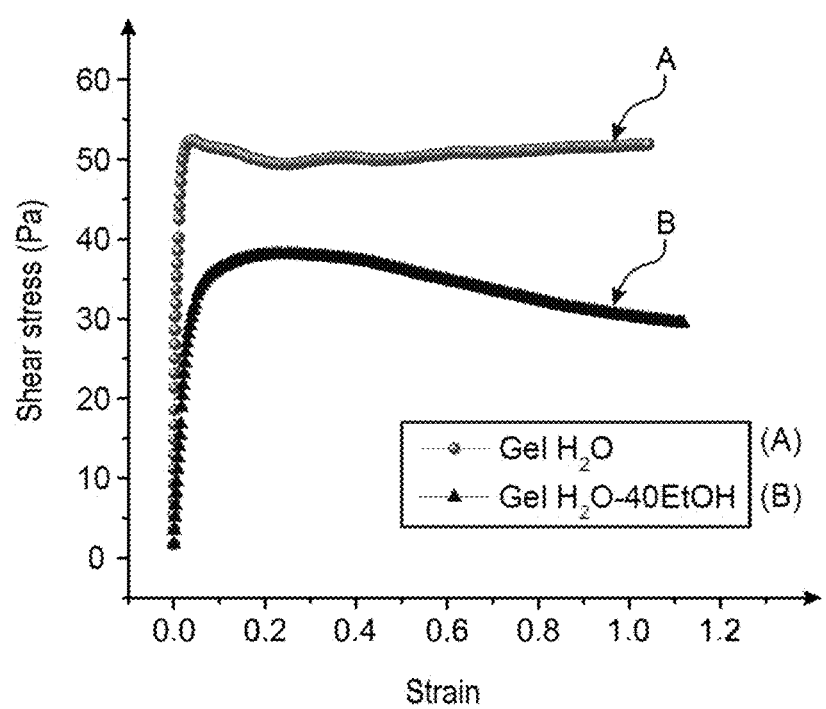

FIG. 6 is a graph giving the change in shear stress as a function of strain of the «$H_2O$ gel» (Curve A) and of the «$H_2O$-40EtOH gel» (Curve B) (see Example 8).

Strain (no unit) is given along the X-axis and shear stress (in Pa) along the Y-axis.

Figure 7:
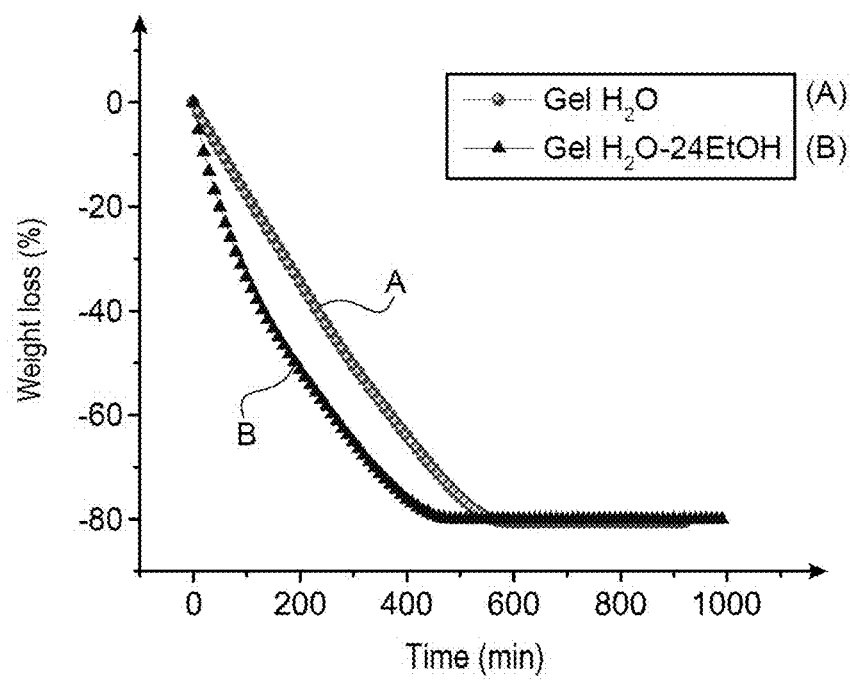

FIG. 7 is a graph illustrating the change in loss of weight as a function of time for the «$H_2O$ gel» (Curve A), and of the «$H_2O$-24EtOH gel» (Curve B) at 25° C. and 50% relative humidity (see Example 11).

Figure 8:
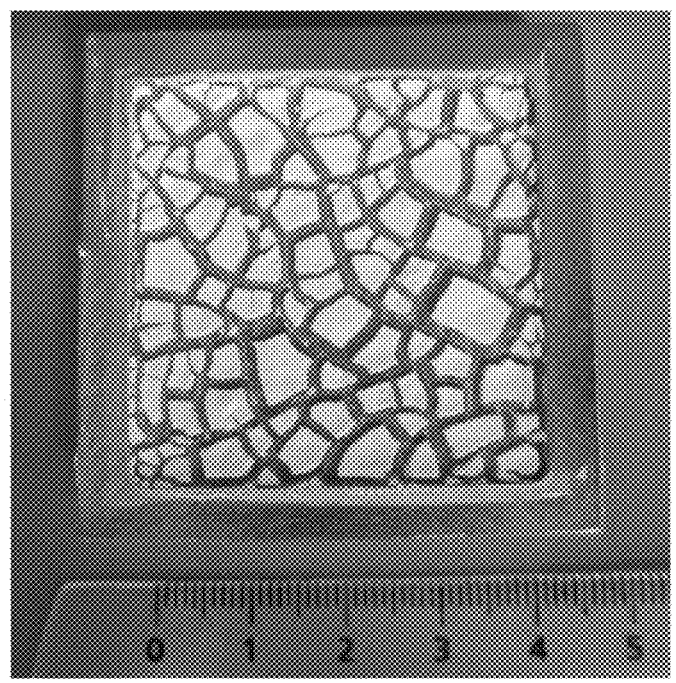

FIG. 8 is a photograph of the flakes obtained after drying the «$H_2O$-24EtOH gel» in a boat of 2 mm depth (see Example 11).

Figure 9:
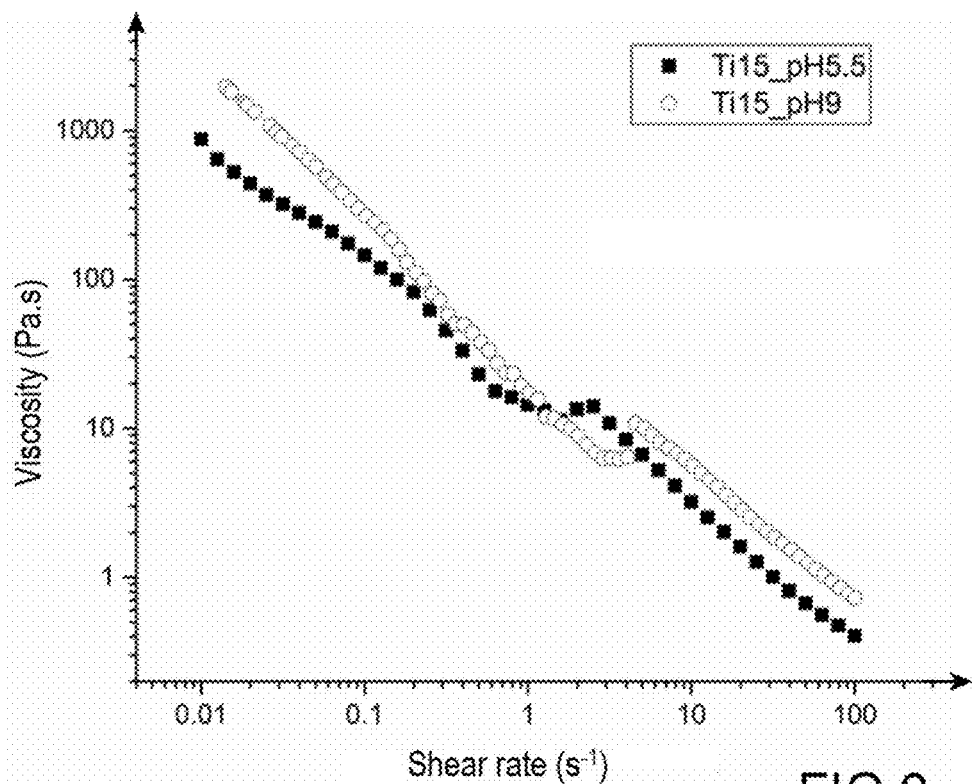

FIG. 9 is a graph illustrating the change in viscosity as a function of shear rate for the gels studied in Example 9.

The shear rate (in $s^{-1}$) is given along the X-axis and the viscosity (in Pa·s) is given along the Y-axis.

Figure 10:
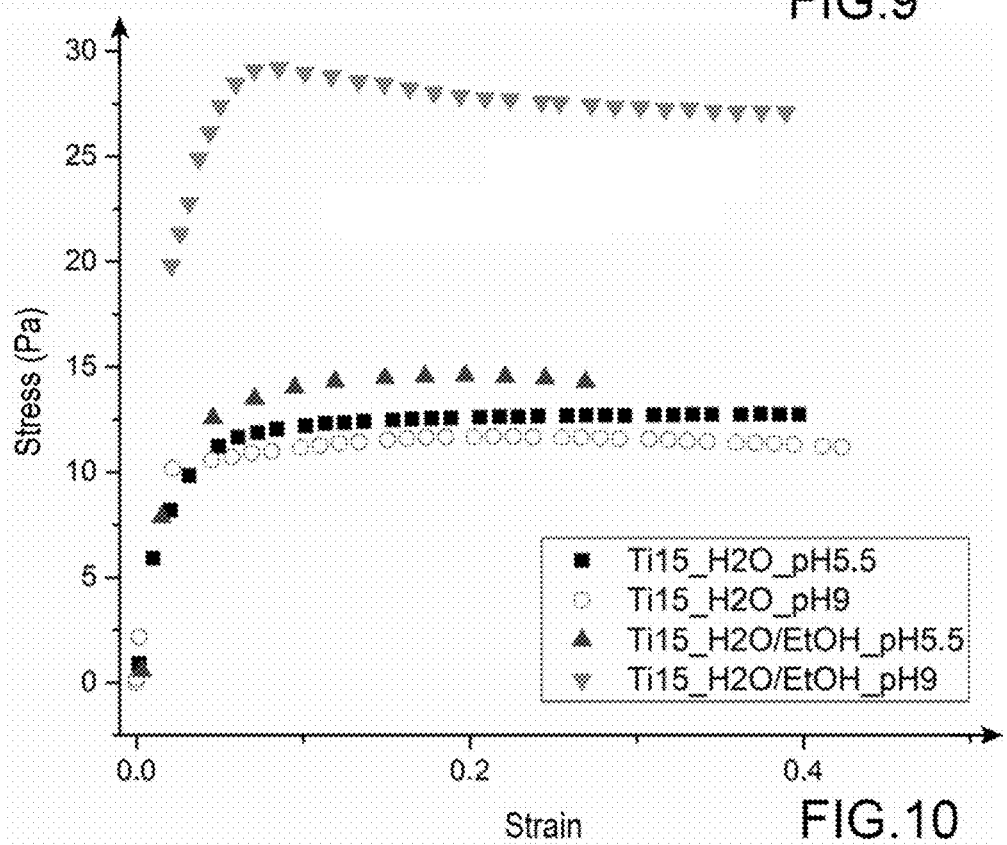

FIG. 10 is a graph illustrating the change in shear stress as a function of strain for the gels studied in Example 10.

Strain (no unit) is given along the X-axis and shear stress (in Pa) is given along the Y-axis.

DETAILED DESCRIPTION OF PARTICULAR EMBODIMENTS

The gel of the invention can easily be prepared at ambient temperature.

For example, the gel of the invention can be prepared by dispersing, preferably gradually, the desired quantity of inorganic viscosifying agent(s), namely $TiO_2$, in the form of particles e.g. of mean diameter 2 to 200 nm in the solvent of the gel.

This dispersion can be obtained via mechanical agitation e.g. with a mechanical agitator equipped with a three-blade impeller. The rotation speed is 200 rpm for example and agitation time 3 to 5 minutes for example.

After dispersion, an opaque white liquid suspension is obtained generally having a pH of about 3.5.

The pH is then gradually increased, under continued agitation, using a base e.g. sodium hydroxide 0.1 M NaOH, until the pH reaches 5 for example which will allow an opaque white viscous gel to form.

When adding the base e.g. sodium hydroxide, the speed of agitation is gradually increased as and when the viscosity increases to arrive at about 400 to 600 rpm without any splashing. The gel is left under agitation for 2 to 5 minutes for example to obtain a fully homogeneous gel.

It is noted here that the amount of base added e.g. sodium hydroxide can be considered to be negligible relative to the initial amount of solvent, and it can therefore be considered that the initial weight composition of $TiO_2$ and of solvent remains valid once pH=5.

The pH of the gel thus prepared is therefore weak acidic since it is 5.

By continuing to increase the pH up to a pH of 7, it is possible to obtain a neutral gel conforming to the invention which therefore prevents chemical attack of the treated surfaces, and even a weak basic gel conforming to the invention at a slightly basic pH of above 7 to less than 9, or even a very basic gel conforming to the invention at a very basic pH of 9 or higher which therefore has degreasing properties, power, but does not attack the treated surfaces.

In the neutral gel and weak basic gel, but also in the very basic gel, the amount of sodium hydroxide can generally always be considered to be negligible.

In general, the gel of the invention must have a viscosity of less than 200 mPa·s under shear of 1000 $s^{-1}$ to allow spraying onto the surface to be decontaminated, at a distance (e.g. at a distance of 1 to 5 m) or close thereto (e.g. at a distance of less than 1 m, preferably 50 to 80 cm).

The viscosity reset time is generally less than one second, and viscosity under low shear is higher than 10 Pa·s so as not to run off on a vertical wall.

The gel of the invention thus prepared is applied to the solid surface to be decontaminated of a substrate or solid material, in other words onto the surface having been exposed to contamination e.g. to a biological contamination.

This contamination has already been described above. In particular, biological contamination may consist of one or more biological species already defined above.

As already indicated above, in the gel of the invention $TiO_2$—in addition to the role of inorganic viscosifying agent—acts as active decontamination agent e.g. active biological decontamination agent, allowing the removal, destruction or inactivation of a polluting, contaminating species e.g. a biological contaminating species.

There is no limitation as to the constituent material of the surface to be decontaminated, the gel of the invention allowing the treatment of all kinds of materials even fragile materials without any damage.

Even surfaces in materials such as alloys of light metals of aluminium type which could not be treated without being deteriorated by prior art gels, can be successfully treated with the gels of the invention.

The gel of the invention does not generate any deterioration, erosion, chemical mechanical or physical attack of the treated material. The gel of the invention is therefore not in any manner detrimental to the integrity of the treated materials and even allows reuse thereof. For example, sensitive equipment such as military equipment is preserved and can be reused after decontamination, whilst monuments treated with the gel of the invention are absolutely not degraded and have their visual and structural integrity preserved.

This material of the substrate can therefore be selected for example from among metals and alloys such as stainless steel, aluminium and lead; polymers such as plastic materials or rubbers among which mention can be made of PVC, PP, PE in particular HDPE, PMMA, PVDF, PC; glass; cements and cement materials; mortars and concretes; plaster; bricks; natural or artificial stone; ceramics.

In all cases, irrespective of the material, the decontaminating efficacy by the gel of the invention is complete.

The treated surface can be painted or non-painted.

The gel of the invention is just as effective on porous materials such as cementitious matrices e.g. pastes, mortars and concretes, bricks, plaster or natural or artificial stone.

The efficacy of treatment with the gel of the invention is generally total including on materials contaminated to a depth of several microns (see above).

There is also no limitation as to the shape, geometry and size of the surface to be decontaminated, the gel of the invention and the method implementing the gel allowing the treatment of surfaces of large size, complex geometry for example having hollows, corners, recesses.

The gel of the invention ensures efficient treatment not only of horizontal surface such as floors but also of vertical surfaces such as walls, partitions or inclined or overhanging surfaces such as ceilings.

Compared with existing decontamination methods e.g. biological decontamination methods using liquids such as solutions, the decontamination method of the invention which uses a gel is particularly advantageous to treat materials of large surface area that cannot be transported or are installed outside. Since the method the invention uses a gel it allows in situ decontamination, preventing the spilling of chemical solutions into the environment and the dispersion of contaminating species.

The gel of the invention may be applied to the surface to be treated using all applications methods known to the man skilled in the art.

Conventional methods are spraying e.g. with a gun or application with a brush or float.

For application by spraying the gel of the invention onto the surface to be treated, the colloidal solution can be conveyed for example via a low pressure pump e.g. a pump which applies a pressure of 7 bars or less i.e. about $7 \cdot 10^5$ Pascals.

The jetting of the gel on the surface can be obtained using flat jet or round jet nozzle for example.

There may be any distance between the pump and the nozzle e.g. it can be 1 to 50 m, in particular 1 to 25 m.

The sufficiently short reset time of the viscosity of the gel of the invention allows the sprayed gels to adhere to all surfaces e.g. to walls.

The quantity of gel deposited on the surface to be treated is generally 100 to 2000 g/m$^2$, preferably 500 to 1500 g/m$^2$, more preferably 600 a 1000 g/m$^2$.

The quantity of gel deposited per unit surface area and hence the thickness of the deposited gel has an impact on the drying rate.

Therefore, when a film, a layer of gel is sprayed of thickness 0.5 mm to 2 mm onto the surface to be treated, the efficient contact time between the gel and the surface is then equivalent to its drying time, the period during which the active ingredient contained in the gel, here TiO$_2$, will interact with the contamination.

In the case of porous substrates e.g. cementitious matrices the action time of the decontamination solution, e.g. of the biocidal solution having penetrated into the core of the material, can be longer than the gel drying time in which case it is generally necessary either to carry out rewetting with the decontamination solution or to repeat gel spraying.

In addition, it has surprisingly been shown that the quantity of deposited gel when it lies within the above-mentioned ranges and in particular when it is 500 g/m$^2$ and higher and particularly within the range of 500 to 1500 g/m$^2$, which corresponds to a minimum thickness of deposited gel e.g. 500 μm or thicker for a quantity of deposited gel of 500 g/m$^2$ or higher, allows fractionating of the gel after drying into the form of vacuumable millimetre flakes e.g. of size 1 to 10 mm, preferably 2 to 5 mm.

The quantity of deposited gel, and hence the thickness of deposited gel, preferably of 500 g/m$^2$ or higher i.e. 500 μm, more preferably 1000 g/m$^2$ or higher i.e. 1000 μm (1 mm) is the fundamental parameter which impacts the size of the dry residues formed after drying of the gel, and which therefore ensures dry residues of millimetric size to be formed and not powdery residues, the former being easily removed via mechanical means and preferably by vacuuming, suction.

The gel is then maintained on the surface to be treated for the entire period of time that is required for drying. Throughout this drying step, which can be considered as forming the active phase of the method of the invention, the solvent contained in the gel, e.g. the water contained in the gel is evaporated until a dry solid residue is obtained.

Drying time is dependent on the composition of the gel within the concentration ranges of the constituents thereof given above, but also as already specified on the quantity of gel deposited per unit surface area i.e. on the thickness of the deposited gel.

Drying time is also dependent on weather conditions, namely temperature and relative humidity of the atmosphere surrounding the solid surface.

The method of the invention can be implemented under extremely wide weather conditions namely at a temperature T of 1° C. to 50° C. and relative humidity RH of 20% to 80%.

The drying time of the gel of the invention is therefore generally 1 hour to 24 hours at a temperature T of 1° C. to 50° C. and relative humidity HR of 20% to 80%. The gel applied to the contaminated surface may be exposed to a light radiation during the drying time.

Light radiation can be visible radiation or A, B or C ultraviolet radiation produced by a UV lamp for example. For example, the gel applied to the surface can be exposed to UV radiation at a wavelength of 365 nm.

The exposure time to radiation which corresponds to the drying time is generally 1 to 24 h. Drying may be accelerated by this UV exposure.

The contaminating species present on the surface is first absorbed within the gel by solubilisation, diffusion and adsorption on the surface of the TiO$_2$ particles.

It is then the photocatalytic property of TiO$_2$ which will allow the destruction and/or inactivation and/or degradation of the contaminating species e.g. the reduction of a multi-valent element (changeover from hexavalent chromium to trivalent chromium for example), the degradation of a chemical contaminating species (organic molecule), or activation of the biocidal property of TiO$_2$, throughout drying.

At the end of drying, the contaminating species is destroyed and/or inactivated and/or degraded and/or absorbed and/or adsorbed.

In particular, the toxicity of the contaminating species is drastically, even fully annihilated.

After drying of the gel, the contamination e.g. the inactivated biological contamination is removed upon recovering the dry gel residue as described below.

After drying of the gel, the gel fractionates homogeneously to give millimetric dry solid residues e.g. of size 1 to 10 mm, preferably 2 to 5 mm that are non-powdery and generally in the form of solid flakes.

The dry residues may contain the one or more inactivated contaminating species.

The dry residues such as flakes obtained after drying have scarce adherence to the surface of the decontaminated material. On this account, the dry residues obtained after drying of the gel may easily be recovered by simple brushing and/or vacuuming, suction. However, the dry residues can also be evacuated by a jet of gas e.g. a jet of compressed air.

Therefore, no rinsing with a liquid is generally necessary and the method of the invention does not generate any secondary effluent.

It is possible however, although not preferred, and if desired, to remove the dry residues by means of a jet of liquid.

The method of the invention therefore first achieves major savings in chemical reagents compared with a decontamination method entailing washing with a solution. Also, since a waste is obtained in the form of a directly vacuumable dry residue, a rinsing operation with water or liquid which is generally needed to remove traces of chemical agents from the part, is generally avoided. The result is evidently a reduction in the amount of effluent produced but also notable simplification in terms of the waste treatment and disposal outlet chain.

On account of the mainly mineral composition of the gel of the invention and low quantity of waste produced, the dry waste can be stored or directed towards an evacuation channel (disposal outlet) without prior treatment.

On completion of the method of the invention, a solid waste is recovered in the form of flakes that can be packaged as such, directly packable; the result, as indicated above, is a signification reduction in the amount of effluent produced and notable simplification in terms of the waste treatment and disposal chain.

In addition, in the nuclear sector, the fact that the flakes do not need to be retreated before packaging of the waste amounts to a considerable advantage; this permits the use of high-performing active agents prohibited up until now in decontamination liquids on account of the operating restrictions for liquid effluent treatment plants (LETPs)

For example, in the routine case in which 1000 grams of gel are applied per m2 of surface area, the weight of dry waste produced is less than 200 grams per $m^2$.

The invention will now be described with reference to the following examples that are non-limiting and given for illustration purposes.

EXAMPLES

Example 1

In this example, weak acidic, neutral or basic gels are described based on $TiO_2$, ($TiO_2$ gel) used in Examples 2, 3, 4, 6 and 7.

The weak acidic based on $TiO_2$ gel was a gel having the following composition in weight percent:
20% $TiO_2$;
80% distilled water.

The $TiO_2$ was $TiO_2$ marketed by Aerosil® under the trade name Degussa P25®.

This gel was prepared in the following manner:

First, the $TiO_2$ particles were dispersed in water using a mechanical stirrer equipped with a three-blade impeller at a speed of 200 rpm.

An opaque white liquid suspension was obtained having a pH of about 3.5.

The pH was gradually increased with 0.1. M NaOH, under continued agitation, until the pH reached 5 which allowed an opaque white viscous gel to be formed.

When adding the sodium hydroxide, agitation was gradually increased as and when viscosity increased, to reach about 400 to 600 rpm without splashing. The gel was then left under agitation for 5 minutes.

It is noted here that the amount of sodium hydroxide added is systematically negligible compared with the initial amount of water, and it can be considered that the weight composition of 20% $TiO_2$ and 80% $H_2O$ remains valid once the pH=5.

The pH of the gel thus prepared is therefore weak acidic since it is 5.

By continuing to increase pH up to a pH of 7, it is possible to obtain a neutral gel which therefore prevents chemical attack of the treated surfaces, and even a very basic gel with a pH of 9 or higher conforming to the invention which therefore has degreasing properties, power.

In the neutral gel and very basic gel, the amount of sodium hydroxide can always be considered to be negligible.

Example 2

In this example, the efficacy of the decontamination of smooth surfaces is shown using a gel prepared in Example 1 containing $TiO_2$.

The decontamination test was conducted on smooth surfaces polluted with Cr(VI), using a $TiO_2$ gel prepared in Example 1.

The smooth surfaces were a ceramic surface, an aluminium surface and a high density polyethylene surface (HDPE).

The test on the smooth surface in ceramic used a ceramic tile and 0.25 ml of $10^{-2}$M $K_2Cr_2O_7$ solution (from Sigma-Aldrich® having 99.0% purity, dissolved in $H_2O$), equivalent to a $2·10^{-2}$M concentrated solution of Cr(VI), were deposited on the ceramic tile.

The drop was left to dry overnight. A yellow spot was obtained on which the acid gel (pH=5) prepared in Example 1 was deposited, the application being performed in the dark to a thickness of 1.25 mm.

The gel was left to dry in the dark to halt any reduction via photocatalysis of Cr(VI) by $TiO_2$, so that only the phenomenon of sorption in the gel could be observed. After a drying time of 4 h30, the dry gel flakes were recovered by brushing. The yellow spot had fully disappeared from the substrate and the gel flakes had become a yellow colour (the characteristic colour of hexavalent chromium), proof that the chromium had indeed been absorbed within the flakes.

The flakes were then dissolved in pure hydrofluoric acid under mechanical agitation at 80° C., for several hours. The solution obtained was analysed by Inductively Coupled Plasma—Optical Emission Spectroscopy» (ICP-OES) using ThermoFisher Scientific apparatus, iCAP 6000 Series®.

The results obtained are given in Table 1 below.

It is noted here that the initial weight of hexavalent chromium deposited on the substrate was 0.26 mg.

TABLE 1

| ICP-OES results obtained after dissolution of the gel flakes in Example 2. | | | |
|---|---|---|---|
| Weight of flakes | HF total volume | Chromium weight determined by ICP | % decontamination |
| 567 mg | 105 mL | 0.26 mg | 100% |

It is observed that the $TiO_2$ gel fully decontaminates the ceramic tile contaminated with Cr(VI).

The same decontamination test as on a smooth ceramic surface was performed but this time on an aluminium surface and on a smooth surface made of high density polyethylene (HDPE) contaminated with Cr(VI).

The experimental protocol was the same as described above for decontamination of the smooth ceramic surface.

In each case, all the chromium was captured by the gel flakes, leading to 100% decontamination efficacy.

The $TiO_2$ gel therefore indeed allows full decontamination of hexavalent chromium on a smooth surface, irrespective of the material constituting of this surface.

Example 3

In this example, the retaining (confining) properties of ionic pollution are shown after decontaminating a surface with a gel based on $TiO_2$.

More exactly, the purpose in this example was to show the capability of an acid gel (pH=5) based on $TiO_2$, such as described in Example 1, to confine hexavalent chromium in the flakes of dried gel.

These properties, this confining, retaining capability of the $TiO_2$ gel were compared with those of a comparative gel based on $SiO_2$.

The comparative gel based on $SiO_2$ ($SiO_2$ gel) was a gel having the following composition in weight percent:
12% silica;
88% distilled water.

The silica was commercial silica from EVONIK® under the trade name Aerosil®.

The comparative $SiO_2$ gel was prepared in the following manner:

The silica was gradually added to the distilled water under mechanical agitation using a mechanical agitator equipped with a three-blade impeller, at a speed of 200 rpm. When adding the silica, agitation was gradually increased as and when viscosity increased to reach about 400 rpm without any splashing. The gel was left under agitation for 5 minutes.

The pH of this gel was 4.5.

A decontamination test was then performed with the $TiO_2$ gel. Initially the operating protocol of this test was the same as in Example 2, namely: 0.25 mL of $10^{-2}M$ $K_2Cr_2O_7$ solution (from Sigma-Aldrich, having 99.0% purity, dissolved in $H_2O$), equivalent to a $2 \cdot 10^{-2}M$ concentrated solution of Cr(VI), were deposited on a ceramic tile.

The drop was left to dry overnight.

A yellow spot was obtained on which the $TiO_2$ gel prepared in Example 1 was deposited and applied in the dark (to prevent reduction of the chromium via photocatalysis) to a thickness of 1.25 mm.

The gel was left to dry in the dark to halt any reduction via photocatalysis of Cr(VI) by $TiO_2$ and so that only the phenomenon of sorption within the gel is observed.

After a drying time of 4 h30 the following protocol was applied:

all the flakes were collected and re-dispersed in 20 mL of $H_2O$ under mechanical stirring using a magnetic stir bar 2 h. The flakes were thus leached in $H_2O$. In theory, if the entirety of the chromium contained in the flakes was released, this will give a solution of $[Cr(VI)]_0 = 2.5 \times 10^{-4}M$.

This value of $[Cr(VI)]_0 = 2.5 \times 10^{-4}M$ is obtained as follows: 0.25 mL of dried $2 \cdot 10^{-2}M$ solution of Cr(VI) that is finally found in 20 mL i.e. $(0.25 \times 2 \cdot 10^{-2})/20 = 2.5 \times 10^{-4}$.

the suspension obtained was then centrifuged for 30 minutes at 4400 rpm and finally filtered through a 0.22 μm filter.

Figure 1:
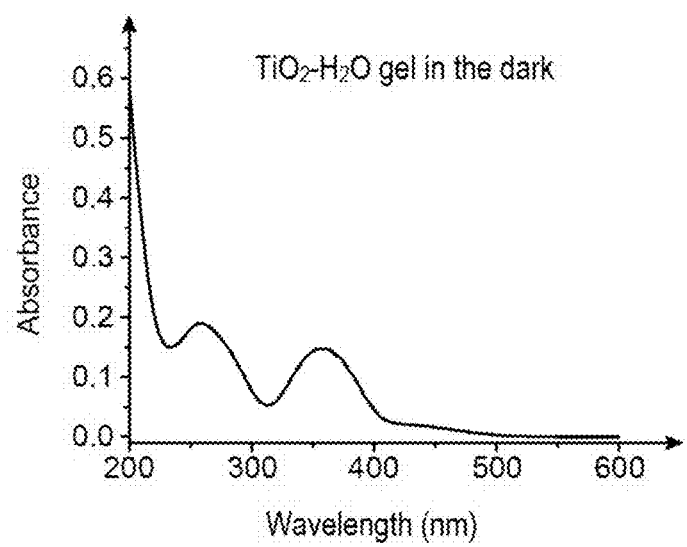
FIG. 1 is a graph illustrating the UV-Visible spectrum of the solution obtained in Example 3 after leaching of the flakes of a $TiO_2$-based gel, namely the gel prepared in Example 1 in which the solvent is water and which was applied and dried in the dark.

These steps allowed complete separation of the $TiO_2$ particles and gave a leachate containing the species weakly bonded to the gel flakes.

the leachate was analysed with a UV-Visible UV-1800 spectrometer by Shimadzu®, previously calibrated. Calibration was performed using different solutions of $K_2Cr_2O_7$ of known concentrations, and the baseline was obtained on ultrapure water. The absorption spectrum of hexavalent chromium, in an acid medium, showed peaks at the wavelengths 260 nm and 352 nm.

the spectrum for the leachate obtained from $TiO_2$ gel flakes is given in FIG. 1.

Beer-Lambert's law gives access to the concentration of Cr(VI) contained in the analysed solution.

In this example, the test (i.e. application of the gel followed by drying of the gel and re-dispersion) having been performed in the dark, all the Cr was necessarily in the form of Cr(VI). The chromium released by the flakes was therefore present in the leachate, and the content of Cr(VI) in the leachate ([Cr(VI)] (leachate)) was compared with the initial Cr(VI) content ($[Cr(VI)]_0$) used for contamination.

Since it was shown that the flakes initially contained all the contamination in this case (see Example 2), these measurements gave the quantity of chromium still present in the flakes after leaching. The results obtained are given in Table 2 below.

TABLE 2

Results obtained after leaching of $TiO_2$ gel flakes.

| Absorbance at 352 nm | [Cr(VI)] (leachate) | [Cr(VI)] (leachate)/$[Cr(VI)]_0$ |
|---|---|---|
| 0.147 | $8.76 \times 10^{-5}M$ | 0.350 |

These results show that even after leaching of the $TiO_2$ gel flakes in $H_2O$ for 2 h, under mechanical agitation, only 35% of the chromium was released into the solution.

The same decontamination test as performed with the $TiO_2$ gel was then conducted with the comparative $SiO_2$ gel following the same protocol, again in the dark.

After drying, re-dispersion of the flakes, centrifugation and filtration, the leachate was analysed by UV-Visible spectroscopy.

The spectrum for the leachate obtained from the $SiO_2$ gel flakes is given in FIG. 2.

The use of Beer-Lambert's law allowed determination of the concentration of Cr(VI) contained in the leachate, and hence the quantity of Cr(VI) still contained in the silica flakes. The results obtained are given in Table 3 below.

TABLE 3

Results obtained after leaching flakes of $SiO_2$ based gel.

| Absorbance at 352 nm | [Cr(VI)] (leachate) | [Cr(VI)] (leachate)/$[Cr(VI)]_0$ |
|---|---|---|
| 0.382 | $2.27 \times 10^{-4}M$ | 0.91 |

These results show that even after 2 h leaching of silica flakes in $H_2O$, under mechanical agitation, 91% i.e. practically all the chromium was released into the solution.

In the light of this example, the comparison between the capability of the $TiO_2$ gel and the capability of the comparative $SiO_2$ gel to retain chromium when the flakes were replaced in solution clearly shows the significant confining property of the $TiO_2$ gel. The confining property of the $TiO_2$ gel is much higher than that of the comparative $SiO_2$ gel. Therefore, the ability of the $TiO_2$ gel to limit release of pollution, in the event of deterioration of the flakes after treatment of contaminated surfaces, is excellent and better than that of the comparative $SiO_2$ gel.

Example 4

In this example, the decontaminating efficacy is shown of a porous surface using a gel based on $TiO_2$ ($TiO_2$ gel).

For comparison, the same decontamination test was conducted using a «conventional» decontamination gel based on $SiO_2$ ($SiO_2$ gel).

More exactly, the purpose in this example was to demonstrate the adsorbing property of a $TiO_2$ gel, in particular on a porous substrate, namely here a substrate made of concrete.

The tested $TiO_2$ gel was the acid gel (pH=5), described in Example 1. It was compared with a $SiO_2$ gel that was described in Example 3.

Initially the operating protocol for the decontamination test was the same as for Example 2. Only the substrate was different: concrete being used instead of the ceramic tile.

After drying and recovery of the flakes of each gel, these were dissolved under mechanical agitation in pure hydrofluoric acid at 80° C. for several hours and the solutions were analysed by Inductively Coupled Plasma—Optical Emission Spectroscopy (ICP-OES) using ThermoFisher Scientific apparatus, iCAP 6000 Series®, to determine the chromium concentrations within these flakes.

The results obtained are given in Table 4 below.

It is noted here the initial weight of hexavalent chromium deposited on each of the substrates was 0.26 mg.

TABLE 4

ICP-OES results obtained after dissolution of the gel flakes obtained in Example 4.

| Gel | Weight of flakes | HF total volume | Chromium weight determined by ICP | % decontamination |
|---|---|---|---|---|
| $TiO_2$-based | 364.8 mg | 55 mL | 0.1 mg | 38% |
| $SiO_2$-based | 342.6 mg | 45 mL | <d.l. | 0% |

<d.l. = lower than the detection limit of the apparatus.

These results therefore show the adsorbing property of the $TiO_2$ gel. On a porous substrate such as concrete, the $TiO_2$ gel allows decontamination at least of part of the chromium contained in the pores of the concrete, contrary to the comparative «conventional» gel not conforming to the invention and based on $SiO_2$ ($SiO_2$ gel).

Example 5

In this example, the photocatalytic effect of the gel of the invention is demonstrated, leading to reduction of Cr(VI) and hence a decrease in the toxicity thereof.

More exactly, the purpose in this example was to demonstrate the impact of UV or visible radiation on the reducing of Cr(VI) toxicity, after decontaminating a surface contaminated with Cr(VI), by applying onto this surface a $TiO_2$ gel of the invention.

For this example, and following Example 7 (in Example 6 there was no measurement of the quantity of Cr, only visual observation), measurement of the quantity of hexavalent chromium contained in the gel was performed after leaching the dry gel flakes with water, followed by UV-Visible analysis applying the protocol described in Example 3.

It is considered that the ratio $[Cr(VI)](leachate)/[Cr(VI)]_0$ represents the reduction (chemical reduction) of total hexavalent chromium.

Although measurement was only performed on about one third of the total chromium contained in the flakes (only 35% of the chromium contained in the flakes was released into solution after leaching with water), it is assumed that the chromium atoms adsorbed on the surface of the $TiO_2$ particles, and still contained within the flakes, have at least the same probability of being reduced as those contained in the leachate.

The gel of the invention used in this example had the following composition:

TABLE 5

Composition of the gel used in Example 5.

| Gel | Weight % of $TiO_2$ | Weight % of $H_2O$ | Weight % of EtOH | pH (initial) | pH (gel) |
|---|---|---|---|---|---|
| Gel $H_2O$-40 EtOH | 20 | 40 | 40 | 3.7 | 5 |

This gel conforming to the invention was prepared as follows:

Initially the $TiO_2$ particles were dispersed in the solvent (water and ethanol) using a mechanical agitator equipped with a three-blade impeller, at a speed of 200 rpm.

An opaque white liquid suspension was obtained having a pH of about 3.5.

The pH was gradually increased with sodium hydroxide 0.1M NaOH, under continued agitation, until the pH reached 5 which allowed the formation of an opaque white viscous gel.

When adding the sodium hydroxide, agitation was gradually increased as and when the viscosity increased to reach about 400 to 600 rpm without any splashing. The gel was then left under agitation for 5 minutes.

It is noted here that the amount of added sodium hydroxide is systematically negligible relative to the quantity of solvents, and it can therefore be considered that the weight composition of 20% $TiO_2$, 40% $H_2O$, and 40% ethanol remains constant once the pH=5.

The pH of the gel thus prepared was therefore weak acidic since it was 5.

The reducing efficacy of the gels in this example was monitored by UV-Visible spectrometry from which the Cr(VI) concentration was determined.

First, 0.25 mL of $10^{-2}$M $K_2Cr_2O_7$ solution (from Sigma-Aldrich® having 99.0% purity, dissolved in $H_2O$), equivalent to a $2.10^{-2}$M concentration of Cr(VI), were deposited on a ceramic tile.

This operation was performed on two separate ceramic tiles.

The drops were left to dry overnight, after which a spot was obtained on each of the tiles.

The gel described above in this example was deposited on the spot of a first ceramic tile and the whole placed under the radiation of an UV lamp (UV lamp by Vilber®, λ=365 nm), the deposited thickness being 1.25 mm.

The gel described above was also deposited to a thickness of 1.25 mm on the spot of the second ceramic tile and the whole left under visible light.

The first sample was left to dry (formed of a yellow spot on which the gel was deposited) for three hours under the radiation of a UV lamp (UV lamp by Vilber®, λ=365 nm), and the second sample in full daylight under visible light.

The dry gel flakes finally obtained were recovered by brushing.

For the gel dried under UV, the flakes appeared slightly green (the characteristic colour in the presence of Cr(III)) or brown, whereas the gel flakes dried in daylight under visible light still have their yellow hues.

Second, the dry gel flakes were re-dispersed in 20 mL of $H_2O$ for one hour.

After centrifugation and filtration, the leachate was analysed by UV-Visible spectroscopy.

The spectra obtained are given in FIG. 3 (for comparison the curve representing the $TiO_2$ gel of Example 1 is given, in which the solvent was solely water and was dried in the dark).

The results obtained after applying Beer-Lambert's law are summarised in Table 6 below.

On the one hand, analysis of the chromium in the leachate showed that the chromium in the leachate corresponded to about 35% of the total chromium contained in the flakes, as shown in Example 3.

On the other hand, the flakes contained all the initial chromium since it was shown that the gel allowed full extraction of the chromium present on the smooth substrate.

Therefore, the proportion of Cr(VI) in the flakes can be estimated with the following equation:

$$\% \text{Cr}(VI)_{in\,flakes} = 100 \times \frac{[\text{Cr}(VI)]_{analysed\,in\,flakes}}{0.35[\text{Cr}(VI)]_0}$$

TABLE 6

Results obtained after leaching of the gel flakes obtained in Example 5.

| Radiation | Absorbance | [Cr(VI)] (leachate) | % Cr(VI) in the gel flakes |
|---|---|---|---|
| UV | 0.001 | 0 | 0 |
| Visible | 0.032 | $1.9 \times 10^{-5}$M | 21.7% |

These results show that the use of UV radiation allows full reduction of hexavalent chromium to be obtained (almost 100%) whereas for the gel left to dry in daylight under visible light only a 78.3% reduction of hexavalent chromium was obtained However, this example evidences the fact that visible radiation allows at least partial activation of the $TiO_2$ particles, since a 78.3% reduction of Cr(VI) was obtained.

Example 6

In this example, the photocatalytic effect is shown of a $TiO_2$ gel on the destruction of a chemical pollutant.

More exactly, the purpose in this example was to demonstrate the photocatalytic property of a $TiO_2$ gel on the degradation of organic compounds.

As organic compound to be destroyed, degraded, an organic dye was used, Methyl Red (Sigma-Aldrich®) in the form of a 40 mg/L solution of this dye.

This organic dye is red at pH values below 4.4, orange at pH values of between 4.4 and 6.2 and yellow at pH values higher than 6.2.

4 drops of the solution of this dye were deposited on a smooth substrate, namely a ceramic tile. The drops were left to dry to obtain 4 spots, and three different gels were deposited using a spatula on three of these spots whilst the last spot was left uncovered, did not receive any gel and therefore acted as control dye spot.

The 3 gels were:

an acidic $TiO_2$ gel (pH=5), such as described in Example 1;

a comparative $SiO_2$ gel such as described in Example 3. This was an acidic gel (pH=4.5);

a comparative $Al_2O_3$ gel. This gel was slightly basic (pH=8).

The comparative $Al_2O_3$ gel was a gel with the following composition in weight percent:

17% alumina;

83% distilled water.

The alumina was the alumina marketed by EVONIK® under the trade name Aeroxide® Alu C.

This comparative gel containing $Al_2O_3$ was prepared in the following manner:

The alumina was gradually added to the distilled water under mechanical agitation using a mechanical agitator equipped with a three-blade impeller at a speed of 200 rpm. When adding the alumina, agitation was gradually increased as and when the viscosity increased to reach about 400 to 600 rpm without any splashing. The gel was then left under agitation for 5 minutes.

The pH of this gel was measured to be 8.

These gels were left to dry under UV radiation (UV lamp by Vilber, λ=365 nm) for 4 h30.

After drying under UV, the control dye spot was intact, the flakes of the comparative $Al_2O_3$ gel, slightly basic, were yellow tallying with the basic nature of this gel, and the flakes of the comparative acidic $SiO_2$ gel were red tallying with the acidic nature of this gel. The organic dye was therefore not degraded by these comparative gels.

On the other hand, the flakes of $TiO_2$ gel were completely white, proving degradation of the organic dye due to the photocatalytic property, power, of $TiO_2$ under UV radiation.

It was therefore demonstrated in this example that it is possible to degrade organic compounds (such as chemical or biological contaminants) present on the surface of a material through the use of a photo-activatable gel based on $TiO_2$.

Example 7

In this example, the impact of the presence of ethanol was examined in $TiO_2$ gels of the invention.

Three gel compositions, including two gel compositions according to the invention, were studied in this example.

These gels were prepared in the same manner as in Example 1 except that for the two last gels prepared, conforming to the invention, the solvent was modified and comprised a mixture of water and ethanol instead of only water (see Table 7 below).

Once again, it can be considered that the weight amounts of added sodium hydroxide are negligible relative to the weights of the solvent(s), and it can therefore be considered that the weight compositions remain constant once pH=5.

TABLE 7

Composition of the gels studied in Example 7.

| Gel | Weight % $TiO_2$ | Weight % $H_2O$ | Weight % EtOH | pH (initial) | pH (gel) |
|---|---|---|---|---|---|
| Gel $H_2O$ | 20 | 80 | 0 | 3.5 | 5 |
| Gel $H_2O$-24 EtOH | 20 | 56 | 24 | 3.7 | 5 |
| Gel $H_2O$-40 EtOH | 20 | 40 | 40 | 3.7 | 5 |

The reducing efficacy, efficiency, of the gels in this example was demonstrated using the same measuring protocol as in Example 5, but only drying under a UV lamp was used.

After drying, re-dispersion of the flakes, centrifugation and filtration, the leachate was analysed by UV-Visible spectroscopy. For each of the examined gels, the colour of the dried flakes was green (characteristic colour of the presence of Cr(III)) or brown, and yellow traces were no longer observed on the substrate.

The UV-Visible spectra are given in FIG. 4 (for comparison, the curve representing the $TiO_2$ gel of Example 1 is added, in said gel the solvent was solely water and it was dried in the dark).

The results obtained by applying Beer-Lambert's law are given in Table 8 below.

The % of Cr(VI) in the flakes was calculated in the same manner as for Example 5.

TABLE 8

Results obtained after leaching the gel flakes obtained in Example 7.

| Gel | Absorbance at 352 nm | [Cr(VI)] (leachate) | % Cr(VI) in gel flakes |
|---|---|---|---|
| Gel $H_2O$ | 0.006 | $3.6 \times 10^{-6}$M | 4.1% |
| Gel $H_2O$-24 EtOH | 0 | 0 | 0 |
| Gel $H_2O$-40 EtOH | 0 | 0 | 0 |

These results show that for the three gel compositions presented in this example, with drying under UV, excellent results were obtained since at least 95.9% of the hexavalent chromium was reduced.

It is noted that the presence of ethanol in the gels of the invention, acting as sacrificial element to prevent electron-hole recombination, allows a slight improvement in the reducing efficacy of the gel to reach a 100% reduction of hexavalent chromium.

Example 8

In this example, it is shown that the gels of the invention can be applied by spraying.

A rheological study was conducted on two of the three gels described in Example 7, namely the «$H_2O$» gel and the «$H_2O$-40 EtOH» gel of the invention, and showed that these gels are suitable for application by spraying.

For application of these gels using a spray method, they must have the properties of a rheofluidifying, thixotropic fluid having a very short reset time (less than one second) and with a threshold stress typically higher than 15-20 Pa.

Different rheological measurements were made using a rheometer by TA Instruments® AR-1000 in vane geometry, and are given in this example.

First, the viscosity of the gel was measured as a function of shear rate. After pre-shearing for 5 minutes at a shear rate of 20 $s^{-1}$ then 1 minute at $6.72 \times 10^{-3}$ $s^{-1}$, several shear rate plateau values were applied ranging from $6.2 \times 10^{-3}$ $s^{-1}$ to 100 $s^{-1}$ measuring viscosity every 30 seconds.

FIG. 5 gives the change in viscosity (Pa·s) of the two gels examined in this example as a function of shear rate ($s^{-1}$) for shear rates of between $6.72 \times 10^{-3}$ and 100 $s^{-1}$.

For each of the gels, a drastic drop in viscosity was observed with shear rate, characteristic of rheofluidifying behaviour.

Additionally, it was found that the presence of ethanol in the gel conforming to the invention tends to make the rheofluidifying behaviour of the gel more perfect. The viscosity value of the «$H_2O$-40 EtOH» gel of the invention as a function of shear rate progresses in a more linear way than that of the «$H_2O$» gel which has jumped in a fairly irregular way.

Also, the threshold stress values of these two gels described in Example 7 («$H_2O$» gel and «$H_2O$-40 EtOH» gel of the invention) were determined by measuring the changes in shear stress and their strain under an imposed shear rate.

A low shear rate ($6.72 \times 10^{-3}$ $s^{-1}$) was constantly applied to each gel to obtain deformation thereof starting from rest, and thereby determine their flow threshold.

FIG. 6 shows shear stress as a function of strain obtained for the two gels described in Example 7.

The two curves have the same shape: two states are observed. First, stress is strongly increased and the material is in solid state (elastic deformation). A change in behaviour is then observed, stress reaches the flow threshold and the material moves into liquid state (stationary flow). The threshold stress then corresponds to the yield stress of the gel i.e. 52 Pa for the «$H_2O$» gel and 36 Pa for the «$H_2O$-40 EtOH» gel. This threshold stress is therefore much higher than 20 Pa which will enable the gel to adhere to a wall in thicknesses of between 0 and at least 2 mm.

To conclude for this example, the $H_2O$ and $H_2O$-40EtOH gels indeed have adequate rheological properties allowing them to be easily sprayed onto different types of surfaces (whether or not horizontal). The presence of ethanol in the gel has a significant impact on the rheology of the gel: first it allows the tending towards a more pronounced rheofluidifying nature, but secondly the gel has a slightly lower threshold stress and will therefore flow more easily.

Example 9

In this example, it is shown that the gels of the invention can be applied by spraying.

For being able to be applied using a spray technique, the gels of the invention must have the properties of a rheofluidifying fluid.

Two gel compositions conforming to the invention were studied in this example.

These gels were prepared in the same manner as in Example 1.

Once again, it can be considered that the weight amounts of added sodium hydroxide are negligible relative to the solvent weights.

TABLE 9

Compositions of the gels studied in Example 9.

| Gel | Weight % $TiO_2$ | Weight % $H_2O$ | Weight % EtOH | pH (initial) | pH (gel) |
|---|---|---|---|---|---|
| Ti15_pH 5.5 | 15 | 42.5 | 42.5 | 3.7 | 5.5 |
| Ti15_pH 9 | 15 | 42.5 | 42.5 | 3.7 | 9 |

Rheological measurements were carried out using a TA Instruments® AR-1000 rheometer in vane geometry, and are given in this example.

The viscosity of the gel was measured as a function of shear rate.

After pre-shearing for 5 minutes at a shear rate of 0.01 $s^{-1}$, several shear rate plateau values were applied ranging from 0.01 $s^{-1}$ to 100 $s^{-1}$ and the viscosity was measured.

FIG. 9 gives the change in viscosity (Pa·s) of the two gels studied in this Example 9 as a function of the shear rate ($s^{-1}$) for shear rates of between 0.01 and 100 $s^{-1}$.

For each of the gels, a drastic drop in viscosity with shear rate was observed, characteristic of a rheofluidifying behaviour.

To conclude this example, it can be said that the two gels in this example, Ti15_pH 5.5 and Ti15_pH 9 are indeed rheofluidifying and can therefore be applied by spraying.

Example 10

In this example, it is shown that the gels of the invention are able to hold, adhere with a thickness of several millimetres onto non-horizontal surfaces such as a wall or ceiling.

To do so, the studied gels must have a sufficiently high flow threshold i.e. a threshold stress higher than 10 Pa.

Four gel compositions were examined in this example. These gels were prepared in the same manner as in Example 1.

Among these four gel compositions, two conformed to the invention namely the gel compositions designated «Ti15_H$_2$O/EtOH pH 5.5» and «Ti15_H$_2$O/EtOH_pH 9».

Once again, it can be considered that the weight amounts of added sodium hydroxide are negligible relative to the solvent weights.

TABLE 10

Compositions of the gels studied in Example 10.

| Gel | Weight % TiO$_2$ | Weight % H$_2$O | Weight % EtOH | pH (initial) | pH (gel) |
|---|---|---|---|---|---|
| Ti15_H$_2$O_pH 5.5 | 15 | 85 | 0 | 3.7 | 5.5 |
| Ti15_ H$_2$O_pH 9 | 15 | 85 | 0 | 3.7 | 9 |
| Ti15_H$_2$O/EtOH_pH 5.5 | 15 | 42.5 | 42.5 | 3.7 | 5.5 |
| Ti15_ H$_2$O/EtOH_pH 9 | 15 | 42.5 | 42.5 | 3.7 | 9 |

The threshold stress values of the gels described in this example were determined by measuring the change in their shear stress and their strain under an imposed shear rate.

Measurements were carried out with a TA Instruments® AR-1000 rheometer in vane geometry, and are given in this example.

A low shear rate (0.01 s$^{-1}$) was constantly applied to each gel to obtain deformation thereof starting from rest, and thereby determine their flow threshold.

FIG. 10 gives the shear stress as a function of the deformation obtained for the four gels described in this example.

The four curves display the same shape: two states are observed. First stress increases strongly and the material is in solid state (elastic deformation).

Thereafter a change in behaviour is observed, stress reaches the flow threshold and the material changes over to liquid state (stationary flow). The threshold stress then corresponds to the yield stress of the gel i.e. 12 Pa for the «Ti15_H$_2$O_pH 5.5» gel and 11 Pa for the «Ti15_H$_2$O_pH 9» gel, 14 Pa for the «Ti15_H$_2$O/EtOH_pH 5.5» gel and 29 Pa for the «Ti15_H$_2$O/EtOH_pH 9» gel. These threshold stresses are therefore much higher than 10 Pa which will enable the gels to adhere to a wall in thicknesses of between 0 and at least 1 mm.

It is additionally observed that the presence of ethanol in the gels of the invention allows an increase in the flow threshold of the gel, and hence the possibility to deposit a greater gel thickness on non-horizontal surfaces such as walls or ceilings.

Example 11

In this example, it is shown that after application and drying, the gels of the invention are vacuumable, suctionable.

More exactly, the purpose in this example was to show that the gels of the invention, described in the preceding examples, dry within a reasonable time of a few hours, that they fractionate producing non-powdery flakes of millimetric size that can be easily vacuumed, suctioned.

The impact of the presence of ethanol is also shown in this example, in particular regarding drying time.

To conduct this study, the «H$_2$O» gel and the «H$_2$O-24 EtOH» gel of the invention were each left to dry in a Binder® climate chamber having a set temperature and relative humidity percentage of 25° C. and 50% respectively.

The gels were spread over a boat made of stainless steel machined to obtain a controlled thickness of 2 mm of gel in the boat.

In the climate chamber, a Sartorius® precision balance was installed together with a Moticam® camera surrounded by a circular LED lamp (VWR) positioned on the top of the balance.

The balance and Moticam® camera were connected to a computer positioned outside the climate chamber allowing simultaneous acquisition, throughout drying under a controlled atmosphere, of the weight and images of the boat filled with gel.

It is to be noted that the weighing boat containing the gel was placed in the precision balance and that all the doors of the balance were closed with the exception of the door opposite the blower which was 3 cm ajar (to maintain the controlled atmosphere within the balance whilst limiting the airflow related to the operating of the climate chamber). Weight recording throughout drying allows monitoring of drying kinetics. All the results are given in FIG. 7.

It is observed that the two gels examined in this example dry well within a maximum time of only a few hours, namely 580 minutes i.e. 9 hours and 40 minutes for the «H$_2$O» gel, and 480 minutes i.e. 8 hours for the «H$_2$O-24 EtOH» gel conforming to the invention.

The presence of ethanol in the gel formulation therefore allows a reduction in gel drying time since the evaporation of ethanol takes place at a lower temperature than the evaporation of water.

With regard to fractionation, a photograph of the dry flakes obtained with the H$_2$O-24 EtOH gel of the invention deposited in a weighing boat of depth 2 mm, is given in FIG. 8.

It can be seen that the number of flakes formed and especially the size thereof conform well since these flakes are of millimetric size and are not powdery.

REFERENCES

[1] Faure, S., et al., "*Procédé de traitement d'une surface par un gel de traitement, et gel de traitement*", 2003, FR-A1-2 827 530.

[2] Faure, S., P. Fuentes, et Y. Lallot, "*Gel aspirable pour la décontamination de surfaces et utilisation*", 2007, FR-A1-2 891 470.

[3] Cuer, F. et S. Faure, "*Gel de décontamination biologique et procédé de décontamination de surfaces utilisant ce gel*", 2010, WO-A1-2012001046.

[4] Ludwig, A., F. Goettmann, et F. Frances, "*Gel alcalin oxydant de décontamination biologique et procédé de décontamination biologique de surfaces utilisant ce gel*", 2013, WO-A1-2014154818.

What is claimed is:

1. Adsorbent and photocatalytic decontamination gel consisting of a colloidal solution comprising:
   15% to 20% by weight of TiO2, optionally doped, relative to the weight of the gel;
   optionally, 0.01% to 10% by weight relative to the weight of the gel of at least one dye and/or at least one pigment;
   optionally, 0.1% to 2% by weight relative to the weight of the gel, of at least one surfactant;
   optionally, 0.05% to 5% by weight relative to the weight of the gel, of at least one super-absorbent polymer;

and the balance solvent, said solvent being selected from among mixtures of water in a proportion of 40% to 56% by weight, and of ethanol, in a proportion of 24% to 42.5% by weight relative to the weight of gel;
and said gel having a pH of 4 or higher.

2. The gel according to claim 1 having a weak acidic pH of 4 to less than 7; or a neutral pH of 7; or a weak basic pH of more than 7 to less than 9; or a very basic pH of 9 or higher.

3. The gel according to claim 1, wherein the pH of the gel is adjusted by the addition of a mineral base.

4. The gel according to claim 1, wherein the TiO2 is in the form of particles of a mean size of 2 to 200 nm.

5. The gel according to claim 1 having a storage time of at least one year.

6. The method for decontaminating at least one surface of a substrate made of a solid material, said surface being contaminated by at least one contaminating species on said surface, wherein at least one cycle is performed comprising the following successive steps:
   a) applying the gel according to claim 1 on said surface;
   b) maintaining the gel on the surface at least for a sufficient time for the gel to absorb the contaminating species, for the contaminating species then to be adsorbed on the surface of the TiO2 particles, and for the gel to dry and form a dry and solid residue containing said contaminating species adsorbed on the surface of the TiO2 particles;
   c) removing the dry and solid residue containing said contaminating species adsorbed in the gel on the surface of the TiO2 particles.

7. The method according to claim 6, wherein the substrate is made of at least one solid material selected from among metals and metal alloys; polymers; glasses; cements and cement materials; mortars and concretes; plasters; bricks; natural or artificial stone; and ceramics.

8. The method according to claim 6, wherein the contaminating species is selected from among ionic, chemical, biological, nuclear or radioactive contaminating species.

9. The method according to claim 8, wherein the contaminating species is an ionic contaminating species selected from among monovalent and multivalent metal ions.

10. The method according to claim 8, wherein the contaminating species is a biological contaminating species selected from among biotoxic species, bacteria, fungi, yeasts, viruses, toxins, pathogenic spores, prions, and protozoa.

11. The method according to claim 8, wherein the contaminating species is selected from among toxic gaseous chemical species.

12. The method according to claim 6, wherein the gel is applied to the surface to be decontaminated in a proportion of 100 g to 2000 g of gel per m2 of surface area, which generally corresponds to a gel thickness deposited on the surface of 0.1 mm to 2 mm.

13. The method according to claim 6, wherein the gel is applied to the solid surface by spraying, with a brush or with a float.

14. The method according to claim 6, wherein during all or part of step a), and/or during all or part of step b), the gel maintained on the surface is exposed to a visible radiation or to a A, B or C Ultraviolet radiation (UVA, UVB or UVC), or to another radiation, to inactivate, and/or degrade, and/or reduce, and/or destroy the contaminating species by photocatalysis.

15. The method according to claim 6, wherein (during step b), drying is carried out at a temperature of 1° C. to 50° C., and under a relative humidity of 20% to 80%.

16. The method according to claim 6, wherein the gel is maintained on the surface for a time of 2 to 72 hours.

17. The method according to claim 6, wherein the dry, and solid residue is in the form of particles of a size of 1 to 10 mm.

18. The method according to claim 6, wherein the dry solid residue is removed from the solid surface by brushing and/or vacuuming, suction.

19. The method according to claim 6, wherein the cycle is repeated 1 to 10 times using the same gel for each cycle, or using different gels for one or more cycle(s).

20. The method according to claim 6 wherein during step b) the gel, before complete drying, is rewetted with a solvent, preferably with the solvent of the gel applied during step a).

21. Adsorbent and photocatalytic decontamination gel consisting of a colloidal solution consisting of:
   15% to 20% by weight of TiO2, optionally doped, relative to the weight of the gel;
   optionally, 0.01% to 10% by weight relative to the weight of the gel of at least one dye and/or at least one pigment;
   optionally, 0.1% to 2% by weight relative to the weight of the gel, of at least one surfactant;
   optionally, 0.05% to 5% by weight relative to the weight of the gel, of at least one super-absorbent polymer;
   and the balance solvent, said solvent being selected from among mixtures of water in a proportion of 40% to 56% by weight, and of ethanol, in a proportion of 24% to 42.5% by weight relative to the weight of gel;
   and said gel having a pH of 4 or higher.

22. The gel according to claim 3, wherein the mineral base is selected from among sodium hydroxide, potassium hydroxide, and mixtures thereof.

23. The method according to claim 6, wherein said surface is further contaminated by at least one contaminating species below said surface, in the depth of the substrate.

24. The method according to claim 7, wherein the substrate is made of at least one metals or metal alloy selected from the group consisting of stainless steel, painted steels, aluminium and lead.

25. The method according to claim 7, wherein the substrate is made of at least one polymer wherein the polymer is a plastic material or a rubber.

26. The method according to claim 25, wherein the plastic material or rubber is selected from the group consisting of poly(vinyl chloride)s, polypropylenes, polyethylenes, high density polyethylenes, poly(methyl methacrylate)s, poly(vinylidene fluoride)s, and polycarbonates.

27. The method according to claim 9, wherein the monovalent and multivalent metal ions are selected from the group consisting of chromium (VI), nickel (II), silver (I), cadmium (II), mercury (II), arsenic (III) and lead (II) ions.

28. The method according to claim 10, wherein the contaminating species is pathogenic spores.

29. The method according to claim 28, wherein the pathogenic spores is spores of Bacillus anthracis.

30. The method according to claim 10, wherein the biological contaminating species is a toxin selected from the group consisting of botulinum toxin or ricin.

31. The method according to claim 10, wherein the biological contaminating species is a Yersinia pestis bacteria.

32. The method according to claim 10, wherein the biological contaminating species is a vaccine virus.

33. The method according to claim 10, wherein the biological contaminating species is a viruses of haemorrhagic fevers.

34. The method according to claim 11, wherein the toxic gaseous chemical species is selected from the group consisting of neurotoxic or blistering gases.

35. The method according to claim 34, wherein the neurotoxic or blistering gases are selected from the group consisting of Sarin or agent GB, VX, Tabun or agent GA, Soman, Cyclosarin, diisopropyl fluorophosphonate (DFP), Amiton or agent VG, Parathion, mustard gas or agent H or agent HD, Lewisite or agent L, and agent T.

36. The method according to claim 17, wherein the particles are flakes.

* * * * *